(12) United States Patent
Banko

(10) Patent No.: US 11,504,271 B2
(45) Date of Patent: Nov. 22, 2022

(54) SURGICAL HAND-PIECE WITH A BOTTOM FLUID TUBE CONVERTIBLE FROM IRRIGATION TO ASPIRATION

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 650 days.

(21) Appl. No.: 16/595,139

(22) Filed: Oct. 7, 2019

(65) Prior Publication Data
US 2020/0046557 A1 Feb. 13, 2020

Related U.S. Application Data

(63) Continuation-in-part of application No. 15/941,366, filed on Mar. 30, 2018, now Pat. No. 11,207,212.

(51) Int. Cl.
| | | |
|---|---|---|
| *A61F 9/007* | (2006.01) | |
| *A61M 3/02* | (2006.01) | |
| *A61B 17/32* | (2006.01) | |

(52) U.S. Cl.
CPC ......... *A61F 9/00745* (2013.01); *A61M 3/022* (2014.02); *A61M 3/0283* (2013.01);
(Continued)

(58) Field of Classification Search
CPC . A61F 9/00745; A61M 3/022; A61M 3/0283; A61M 2210/0612;
(Continued)

(56) References Cited

U.S. PATENT DOCUMENTS

| | | |
|---|---|---|
| 3,812,855 A | 5/1974 | Banko |
| 3,920,014 A | 11/1975 | Banko |

(Continued)

FOREIGN PATENT DOCUMENTS

| | | |
|---|---|---|
| DE | 10 2015 207 150 A1 | 11/2016 |
| WO | WO 2008/118709 A1 | 10/2008 |

OTHER PUBLICATIONS

International Preliminary Report on Patentability in corresponding PCT Application No. PCT/US 2020/012388, dated Jun. 16, 2021.

(Continued)

*Primary Examiner* — Katherine M Rodjom
(74) *Attorney, Agent, or Firm* — Leason Ellis LLP

(57) ABSTRACT

A work tip for an ultrasonic surgical hand piece has a solid knife with a sharp distal edge. A first fluid tube located on one side of the knife and has open ends to receive or discharge fluid. A second fluid tube is located on the other side of the knife and is slidably connected with the knife. The second fluid tube has an opening at a distal end and a smaller side hole. During phacoemulsification the knife is vibrated independent of the fluid tubes. The second fluid tube has irrigation fluid passing from the opening and side hole, and the first fluid tube is positioned so as to receive fluid from the second tube. During I/A cleanup the second fluid tube receives aspiration fluid only through the side hole because the knife is positioned to block the aspiration fluid from entering through the opening.

34 Claims, 21 Drawing Sheets

(52) U.S. Cl.
CPC ............... *A61B 17/320068* (2013.01); *A61B 2017/32007* (2017.08); *A61B 2017/320072* (2013.01); *A61B 2017/320074* (2017.08); *A61B 2017/320084* (2013.01); *A61B 2217/005* (2013.01); *A61B 2217/007* (2013.01)

(58) Field of Classification Search
CPC .. A61B 17/320068; A61B 2017/32007; A61B 2017/320072; A61B 2017/320074; A61B 2017/320084; A61B 2217/005; A61B 2217/007
See application file for complete search history.

(56) References Cited

U.S. PATENT DOCUMENTS

| | | | |
|---|---|---|---|
| 4,007,742 A | 2/1977 | Banko | |
| 4,019,514 A | 4/1977 | Banko | |
| 5,254,082 A | 10/1993 | Takase | |
| 5,359,996 A | 11/1994 | Hood | |
| 5,693,062 A * | 12/1997 | Stegmann | A61F 9/00763 606/166 |
| 5,695,461 A | 12/1997 | Shaible | |
| 5,709,698 A | 1/1998 | Adams | |
| 5,725,498 A | 3/1998 | Janzen et al. | |
| 6,592,541 B1 * | 7/2003 | Kurwa | A61F 9/00745 604/521 |
| 8,951,272 B2 | 2/2015 | Robertson | |
| 9,439,807 B2 | 9/2016 | Koplin | |
| 2002/0111608 A1 * | 8/2002 | Baerveldt | A61F 9/00781 606/49 |
| 2003/0229344 A1 | 12/2003 | Dycus et al. | |
| 2005/0049546 A1 | 3/2005 | Messerly et al. | |
| 2011/0196399 A1 | 8/2011 | Robertson et al. | |
| 2014/0163595 A1 | 6/2014 | Witt et al. | |
| 2014/0276369 A1 | 9/2014 | Banko | |
| 2015/0126994 A1 | 5/2015 | Matsui et al. | |

OTHER PUBLICATIONS

International Search Report and Written Opinion in corresponding PCT Application No. PCT/US 2020/012388, dated Apr. 20, 2020.
Non-Final Office Action in corresponding U.S. Appl. No. 15/941,366, dated Feb. 18, 2020.
International Search Report and Written Opinion in corresponding PCT Application No. PCT/US2020/054389, dated Feb. 4, 2021.
U.S. Appl. No. 15/783,806, filed Oct. 13, 2017, Banko.
International Search Report and Written Opinion in corresponding PCT Application No. PCT/US2019/024910, dated Jun. 24, 2019.
"New Phaco Tip Geometry Balances Power, Suction," *Ophthalmology Times*, Jul. 15, 1992, vol. 17, No. 14, 3 pages.
"Funnel-shaped tip Controls Ultrasound Energy during Phaco," *Ocular Surgery News*, Jul. 1, 1992, vol. 10, No. 13, pages.
Banko, "Dynamics of intraocular flow and ultrasound power," *Ocular Surgery News*, May 1, 1986, 10 pages.
Devine, "Preferred Technigue Employs High-Vacuum," *Ocular Surgery News*, Sep. 15, 1994, vol. 12, No. 18, 2 pages.
Singer, "High Vacuum Phaco System Allows Better Intraocular Control," *Ophthalmology Times*, Sep. 15, 1994, vol. 19, No. 15, 2 pages.
International Preliminary Report on Patentability PCT Application No. PCT/US2019/024910, dated Oct. 6, 2020.

\* cited by examiner

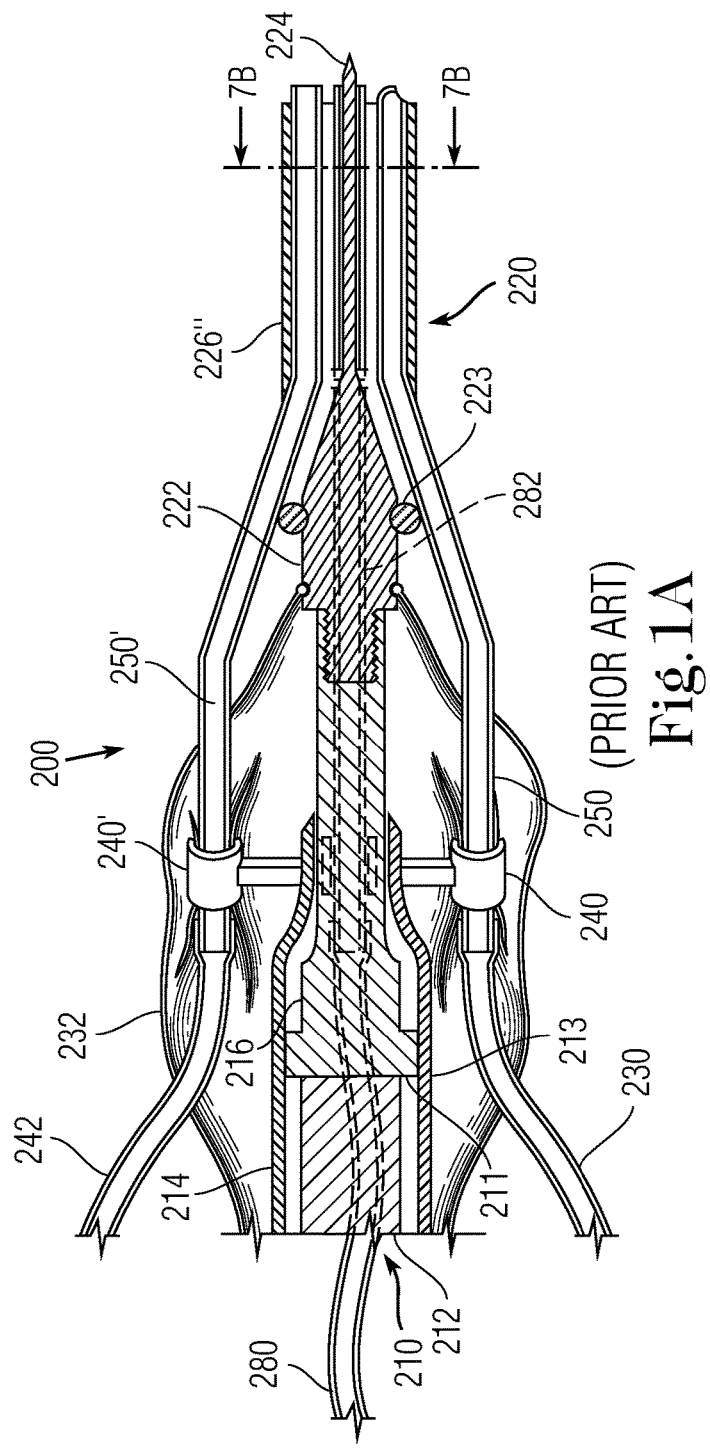
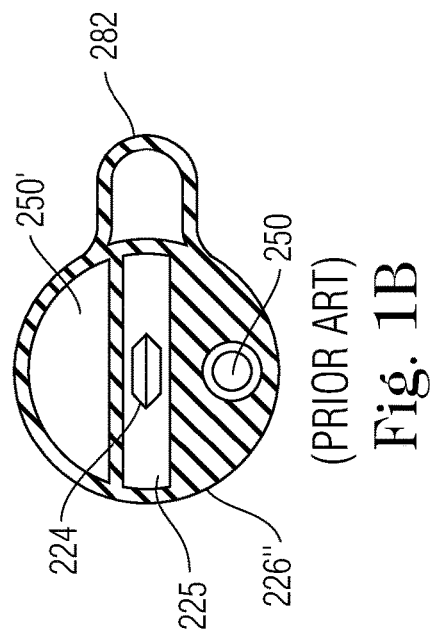
Fig. 1A (PRIOR ART)
Fig. 1B (PRIOR ART)

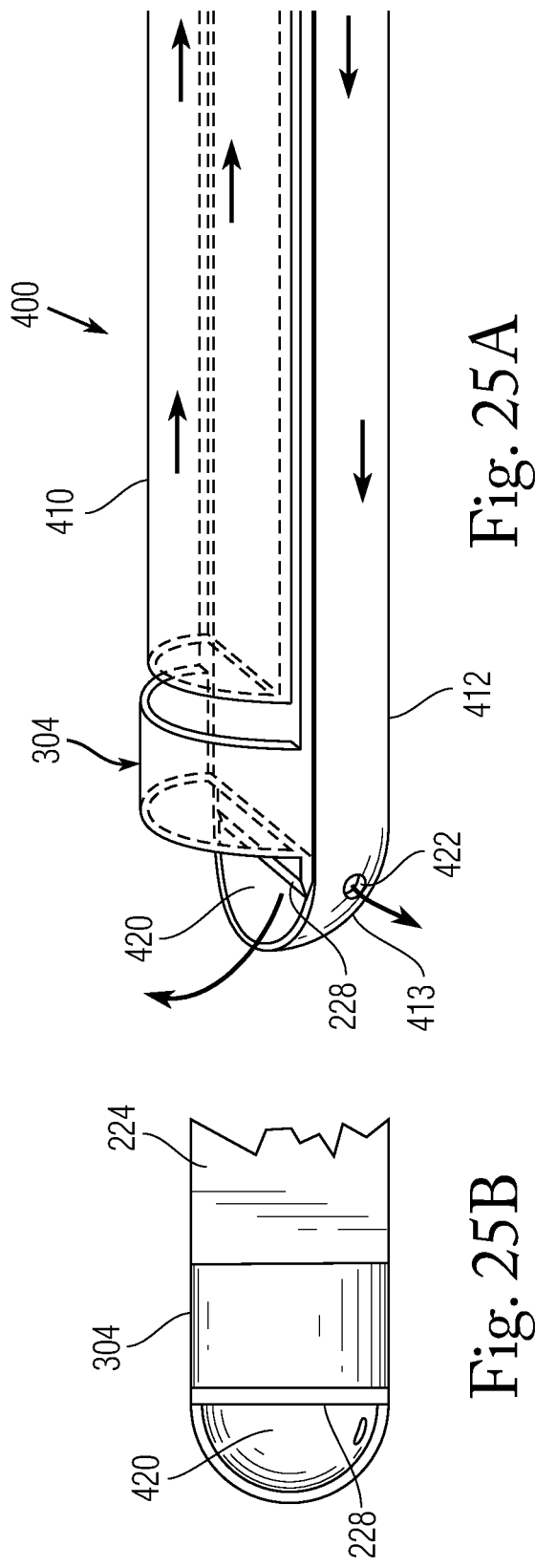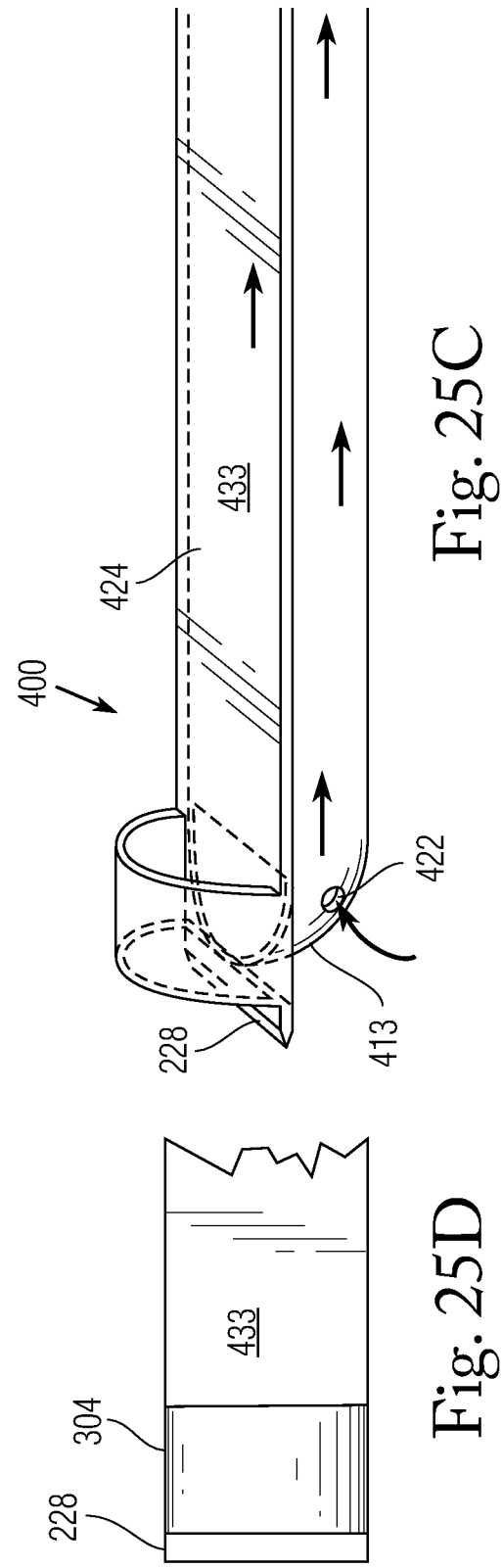

A-A

B-B

SURGICAL HAND-PIECE WITH A BOTTOM FLUID TUBE CONVERTIBLE FROM IRRIGATION TO ASPIRATION

The present invention is a continuation-in-part of U.S. patent application Ser. No. 15/941,366 filed Mar. 30, 2018, the contents of which are incorporated herein by reference in their entirety.

TECHNICAL FIELD

The present invention is generally directed to work tips for surgical hand pieces, particularly work tips with cone shapes for use in the removal of cataracts from the eye of a patient by phacoemulsification.

BACKGROUND OF THE INVENTION

The use of instruments in ocular surgical applications is well known. One widely used type of instrument is an ultrasonic hand piece that is used in ophthalmic applications, such as in the removal of cataracts from the eye by phacoemulsification.

FIGS. 1A and 1B show a work tip for a prior art ultrasonic hand piece as shown in U.S. patent application Ser. No. 15/783,806 filed Oct. 13, 2017 for Dr. William Banko, the present inventor. This design has a handpiece 200 with an ultrasonic vibration part 210 connected to a work tip 220. The vibration part has a housing 214. A transducer 212 is provided in part 210 for generating ultrasonic linear mechanical vibrations upon excitation with an alternating-current electrical signal. The transducer is supported within the housing 214 by flanges 211. A metal connecting body 216 having a reduced diameter distal end portion is attached to the transducer 212. The connecting body forms an acoustic impedance transformer for conveying the longitudinal vibrations of the transducer 212 for application to the operative working tip 220 connected to the distal end of the connecting body 216. Further, the housing has a part 213 that engages the connecting body 216 at a null point in its vibration to provide further support.

The work tip 220 has a hub 222 connected to the distal end of the connecting body 216. The distal end of the hub narrows down to form a solid knife, blade or scalpel 224 with a sharp edge. Flexible tube 230 extracts aspiration fluid from a rigid plastic tube 250 that is located along the blade 224 in the assembled condition. Similarly, a flexible tube 242 provides irrigation fluid to a rigid plastic tube 250' that is located along the blade 224.

A sterile sheet 232 surrounds the vibration part 210, housing 214 and connecting body 216 to isolate them from the non-sterile conditions at the work tip 220. In this design the sheet 232 is attached to the hub 222 of the blade which is detachable from the connecting piece 216. As a result, after an operation the hub can be detached from the work piece and it, the blade and the sheet can be discarded as a one-use product. Since the vibration part 210, housing 214 and connecting body 216 did not come into contact with any tissue or fluids from the last patient and will not contact the tissue or fluids from the next patient, there is no need to sterilize these elements between operations on different patients. As a result, multiple operations can be conducted in a shorter period of time and at less expense.

Rigid tubes 250, 250' are captured in tube holders 240, 240' with the sterile sheet between them. That is, the holders are within the sheet and are not exposed to the operating environment. As shown in FIG. 1B there is a sleeve 226" around the blade 224. This sleeve has channels 250, 250' which are extensions of the plastic tubes 250, 250.' The space 225 for the blade 224 is adjacent to the channels so the blade is adjacent to the fluid channels but does not touch them. Further, sleeve 226" includes a third channel 282 that is located on the side of the work pieces while the irrigation tube 250' is on the top and aspiration tube 250 is on the bottom. The tubes are all located on sleeve 226". The proximal end of the blade channel 225 is blocked by an O-ring 223 so that fluid from the operating site does not pass through this channel of the work tip.

During an operation, the hub 222 and blade 224 of work tip 220 are longitudinally vibrated by the transducer 212. The tubes 250, 250' remain stationary and are supported with respect to the hub and blade by means of the O-ring 223 at the interface between the hub and the tubes. The surgeon places the work tip 220 within the eye and the sharp edge of the blade against the cataract tissue. The ultrasonic vibration of the blade 224 causes the cataract tissue to emulsify. During this process irrigation fluid, e.g., saline solution, is injected into the site from tube/channel 250' since flexible tube 242 is connected to a source of irrigation fluid which may be moved by gravity flow or a pump. Also, the emulsified tissue is removed from the site by aspiration through tube/channel 250 because flexible tube 230 is attached to an aspiration pump. The tube 282 can be used to assist either the irrigation or aspiration flow.

In FIG. 1B the aspiration channel 250 is small compared to the irrigation channel 250'. This can be balanced out using channel 282 to augment aspiration. During an A/I clean up procedure after the cataract has been broken up into little pieces, a low aspiration force is needed to remove the remaining pieces of lens and lens epithelial cells while preventing the tearing of the capsular bag of the eye. Under those circumstances the channel 282 can be closed or used to augment irrigation so that aspiration only occurs though channel 250.

The cross section shown in FIG. 1B has the channel 282 protruding from one side of sleeve 226". Since this structure is required to pass through an incision in the eye, it would be beneficial if the cross section were more uniform but provided the same functional benefits.

Further, there is a prior art work tip known as the "Cobra" tip that has a cone shape. In particular, a cylindrical work tip has an area in which its diameter is increased going from the proximal to the distal end. An early discussion of this tip can be found in the article "New Phaco Tip Geometry Balances Power, Suction," *Ophthalmology Times*, Jul. 15, 1992, Vol. 17, No. 14. As reported in the article the shape concentrates ultrasonic energy within the tip, improving safety and efficiency. In effect the sloped walls of the cone shape provide additional force when the tip is vibrated at ultrasonic rates. See also, the article "Funnel-shaped tip Controls Ultrasound Energy during Phaco," *Ocular Surgery News*, Jul. 1, 1992, Vol. 10, No. 13. It would also be beneficial if the enhanced performance of the Cobra tip could be incorporated into more modern work tips.

During phacoemulsification two types of fluid flow are created in the eye: 1) the irrigation flow from the irrigation tube and 2) the flow created by the ultrasound vibration (pushing fluid forward—with the back and forth vibration of the tip. The backward motion is not enough to cancel the forward pushing of the fluid so there is a net forward flow from the mechanical action of the vibrating tip. The evacuation or aspiration (i.e., the bringing of particles to the tip and removing them through the aspiration tube) must over-come the irrigation and vibration flow. See Banko, "Dynamics of intraocular flow and ultrasound power," *Ocular Surgery News*, May 1, 1986.

Controlling irrigation fluid has two general components: 1) getting irrigation fluid into the eye from an external source and 2) controlling the flow of irrigation fluid within the eye. There are two different ways to get irrigation fluid into the eye, i.e., from a bottle that is hung above the eye so as to create hydrostatic pressure and from a pressurized sterile bottle or bag containing the irrigation fluid. The size and durometer (hardness of the plastic tubes) of the aspiration and irrigation tubes make a big difference in how the fluid is delivered or removed from the eye. For example, a very high negative evacuation pressure (suction) in the eye can only be safely achieved when using a very rigid, small internal diameter tubing for aspiration. If the tubing is not rigid it will collapse with the high suction. Also, the diameter must be small to minimize the volume of fluid removed from the eye (the evacuation flow is better controlled with a small diameter).

When using high suction, the irrigation tubes are the opposite, i.e., they should be soft and flexible to accommodate a large amount of fluid in them at the location of the eye. In particular, for irrigation you want a volume of fluid in the tube. The more flexible the irrigation tubes the more fluid is held in them ready to enter the eye. Also, large diameter irrigation tubes create a larger fluid reservoir within the irrigation tube which can be ready for release into the eye, especially if fluid is removed rapidly with high suction. See Devine, "Preferred Technique Employs High-Vacuum," *Ocular Surgery News*, Sep. 15, 1994 and Singer, "High Vacuum Phaco System Allows Better Intraocular Control," *Ophthalmology Times*, Sep. 15, 1994.

One technique for controlling the direction of flow of irrigation fluid outside of the handpiece is shown in U.S. Pat. No. 5,725,498 of Strukel and Banko in which baffle's can be located on the interior and/or exterior surfaces of irrigation tubes. Similarly, U.S. Pat. No. 9,439,807 of Koplin includes tabs or protrusions on the irrigation tube to direct the irrigation fluid as it leaves the tube. Other patents that disclose the adjustable pressurized control of irrigation fluid in the eye are U.S. Pat. No. 3,812,855 of Banko, U.S. Pat. No. 3,920,014 of Banko; U.S. Pat. No. 4,007,742 of Banko, U.S. Pat. No. 4,117,842 of Banko and U.S. Pat. No. 4,019,514 of Banko.

SUMMARY OF THE INVENTION

In accordance with the invention a surgical hand piece is provided with a solid vibrating blade, knife or scalpel with a sharp cutting edge located in a sleeve with multiple fluid channels, while retaining a uniform cross section. Further, a cobra cone shape is incorporated into the distal end of the blade to improve it efficiency In an illustrative embodiment the surgical hand piece has a solid blade located within a circular sleeve. The sleeve provides irrigation and aspiration channels. Further, the blade may be located in its own channel and may be used to divide that channel into separate irrigation and aspiration fluid flows.

A cone shape may be included at the distal end of the blade. This cone shape in one embodiment interacts with the structure within the sleeve so that in an extended state the work tip performs phacoemulsification, while in a retracted state the aspiration fluid flow path is altered to reduce the flow so that the same work tip can be used for irrigation/aspiration (I/A) cleanup.

In another embodiment, the cone shape tip can be replaced with a cap shape that is open toward the distal side, which generates greater phacoemulsification energy than the cone shape.

A further embodiment has a work tip extending from a sleeve, where a portion of the work tip is in the form of a structure with a half cylindrical main part and a half hemispherical distal end. This structure is provided on the upper surface of a blade. The distal end of the structure has an aspiration cleanup hole in it. During phacoemulsification the blade engages the cataract, irrigation fluid flows out of the sleeve over the upper surface of the blade and around the attachment. Aspiration fluid flows through a collar located under the blade and into the sleeve. During cleanup, the work tip is withdrawn into the sleeve and fluid flow is reversed. In particular, aspiration occurs only through the cleanup hole in the hemispherical distal end and into the sleeve above the blade. Irrigation fluid passes out of the sleeve under the blade and through the collar.

In a still further embodiment, a bottom irrigation tube is loosely attached (so not to dampen vibration) to the underside of the vibrating blade so it can be axially slid along the blade to change its operation. The tube has a large opening in its top surface at the distal end to supply irrigation fluid during phacoemulsification. The irrigation fluid flows through the bottom tube to the site where the sharp edge of the blade is contacting cataract tissue. Channels and baffles at the large opening in the bottom tube direct irrigation fluid out of the large hole in a particular pattern. Directing the irrigation fluid from the tube and within the eye is important to minimize turbulent flow in the eye.

The bottom tube also has a small opening at its lower surface, preferably at its lower distal side surface. After phacoemulsification the tube operation is switched by sliding the blade with respect to the tube so as to close off or block the large opening. Also, the bottom tube is provided with an aspiration force, instead of irrigation fluid, so the small opening can be used for I/A cleanup.

The principles of the invention have numerous advantages. For example, the invention allows for a work tip that is easier to insert into an incision in the eye, but still provides multiple fluid flow paths for use in phacoemulsification and cleanup procedures. It also provides a cone shape to improve the efficiency of the ultrasonic vibrations. By causing the cone shape to interact with a structure in a surrounding sleeve, the work tip function can be changed from phacoemulsification to cleanup without having to remove the work piece from the surgical site, such as the eye, and to replace it with an irrigation/aspiration (I/A) cleanup tool. Further, according to the present invention, cleanup can be commenced without the surgeon having to divert his attention from the eye of the patient.

In addition, the present invention takes into consideration the control and direction of irrigation fluid within the eye by means of various grooves and baffles at the working end of the irrigation tube. This results in a more efficient method of delivering irrigation fluid closer to the vibrating tip and evacuation tube, and assuring a fluid flow that efficiently causes tissue particles created during phacoemulsification to exit the eye through the aspiration tube.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIGS. 1A and 1B are a side view and a cross-sectional view, respectively, of a prior art surgical hand piece with irrigation, aspiration and a third fluid flow path that can be used to augment either of the other two paths;

FIG. 25A is a perspective view of the combined work tip of FIG. 23 with the blade in the retracted position for phacoemulsification, FIG. 25B is a top view of the distal portion of the work tip of FIG. 25A, FIG. 25C is a perspective view of the blade of FIG. 25A in the extended position for I/A cleanup and FIG. 25D is a top view of the distal portion of the work tip of FIG. 25C;

FIGS. 28A and B are a modification of the embodiment of FIGS. 27A and B using one-way valves with a spring hinge instead of a movable sleeve, wherein FIG. 28A shows a cross section of the valve in the open state and FIG. 28B shows the valve in the closed state;

FIGS. 29A and B are a modification of the embodiment of FIGS. 28A and B using one-way valves with a hinge made of tube material instead of a movable sleeve, wherein FIG. 29A shows a cross section of the valve in the open state and FIG. 29B shows the valve in the closed state;

FIGS. 30A and B show a modification of the ninth embodiment of FIGS. 27A and B using one-way valves, wherein FIG. 30A shows a perspective view of the work tip in the phacoemulsification mode and FIG. 30B shows the work tip in the I/A cleanup mode;

DETAILED DESCRIPTION OF THE INVENTION

Figure 2:
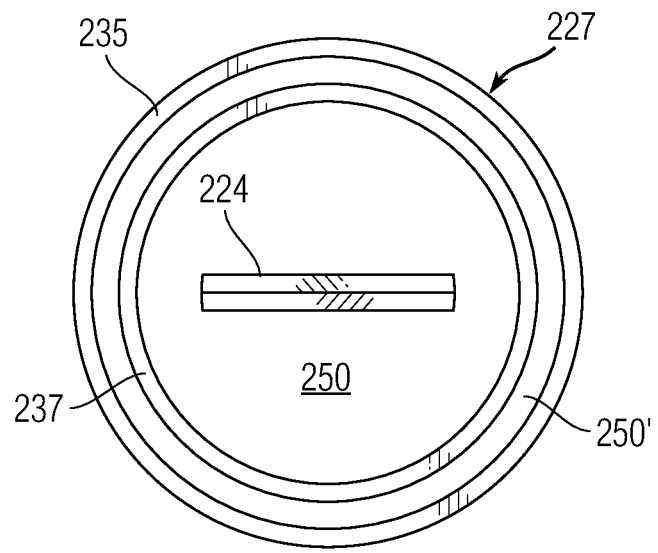
FIG. 2. is cross-sectional view of a blade within an inner channel of a work tip sleeve and a surrounding outer channel according to a first embodiment of the present invention.

FIG. 2 shows an external sleeve 227 in the form of two concentric tubes 235, 237 for a first embodiment of the present invention. The blade 224 is in the center of channel 250 but does not extend completely across the tube 237. With this arrangement irrigation fluid can flow in the channel 250' between the tubes, while aspiration fluid can flow in channel 250 within tube 237.

Figure 3:
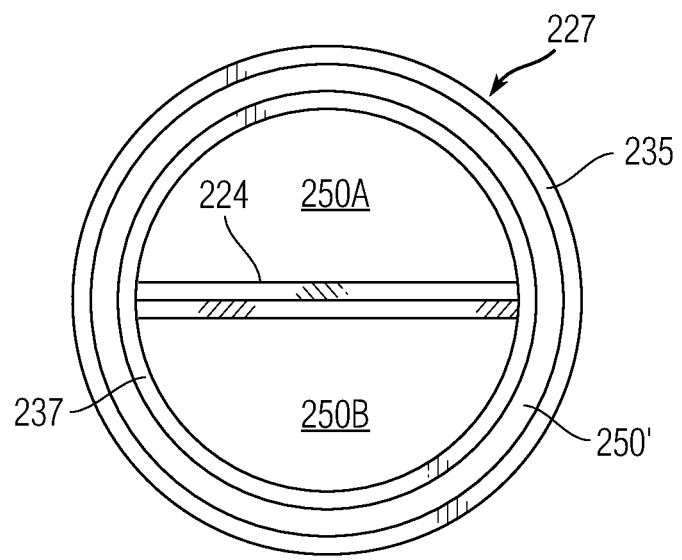
FIG. 3 is a cross-sectional view of a modification of the design of FIG. 2 in which the blade extends completely across the inner channel and divides it into upper and lower channels.

In FIG. 3 the blade 224 extends completely across tube 237 and separates the channel 250 into two distinct chambers, 250A and 250B. Again, the irrigation is in channel 250' between tubes 235, 237. However, because channel 250 has been divided into two channels, there are a total of three channels available that can be alternated or switched by the operation to change the performance. For example, the arrangement can have two aspiration channels and one irrigation channel, or one aspiration channel and two irrigation channels. It should be noted that in FIGS. 2 and 3 the sleeve 227 has a round shape which will make it easier for the surgeon to pass it into an incision in the patient's eye. In particular, it does not have a protrusion like channel 282 in FIG. 1B.

Figure 4A:
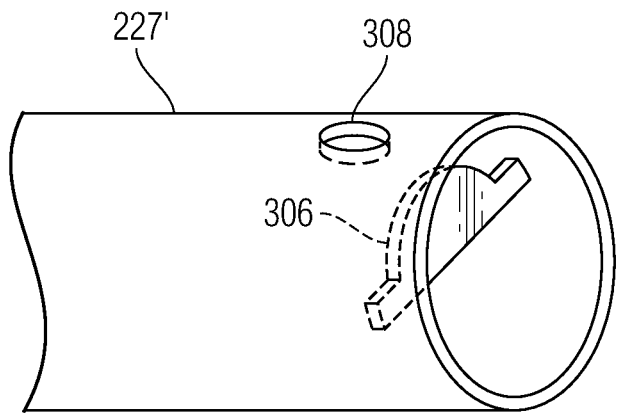
FIG. 4A is a right-side perspective view of the sleeve with an internal structure and hole near its distal end according to a second embodiment of the present invention.
Figure 4B:
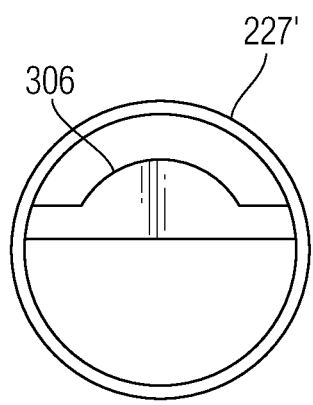
FIG. 4B is a front elevation view of the sleeve and structure of FIG. 4A

In FIG. 4A, which represents a second embodiment of the invention, there is shown a small hole 308 in a single wall sleeve 227'. Because this sleeve has only a single wall, it cannot provide an outer irrigation channel. Instead, the single channel will need to be divided into irrigation and aspiration channels. As will be described in more detail below, the hole 308 can be used as the aspiration opening during cleanup. A structure 306 is shown suspended in the end of sleeve 227' in the upper part. The shape of the structure is best seen in FIG. 4B. Also, the location of the structure with regard to the hole 308 can be determined in FIG. 4C.

Figure 4C:
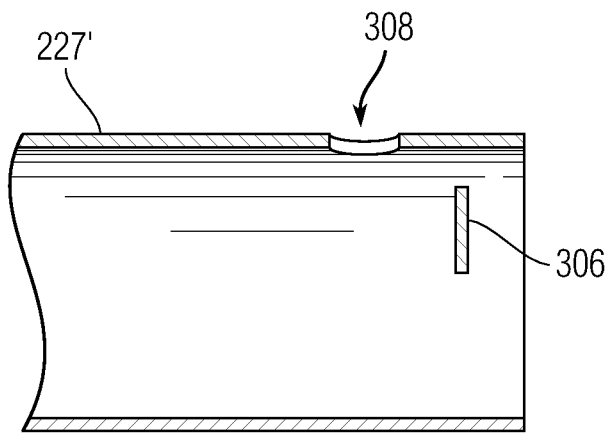
FIG. 4C is a right-side cross-sectional view of the sleeve and structure of FIG. 4A.
Figure 5:
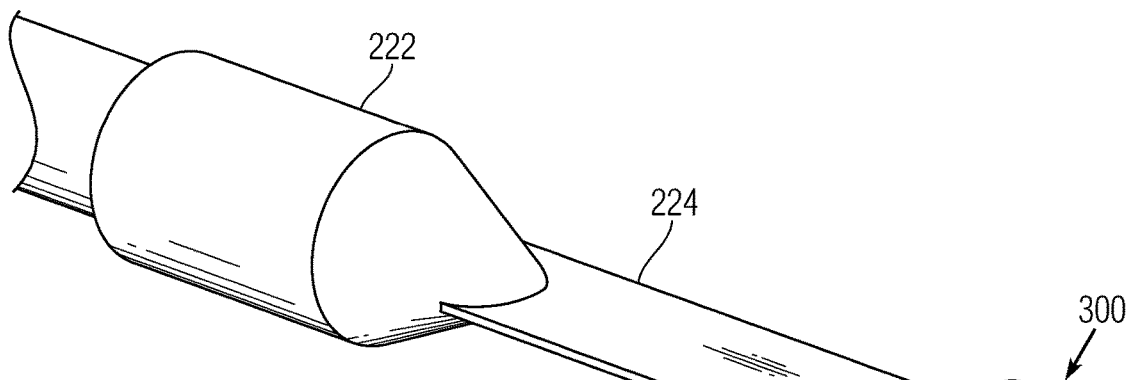
FIG. 5 is a perspective view of the connecting piece attached to a knife blade having a half conical structure at its distal end according to a third embodiment of the present invention.
Figure 6:
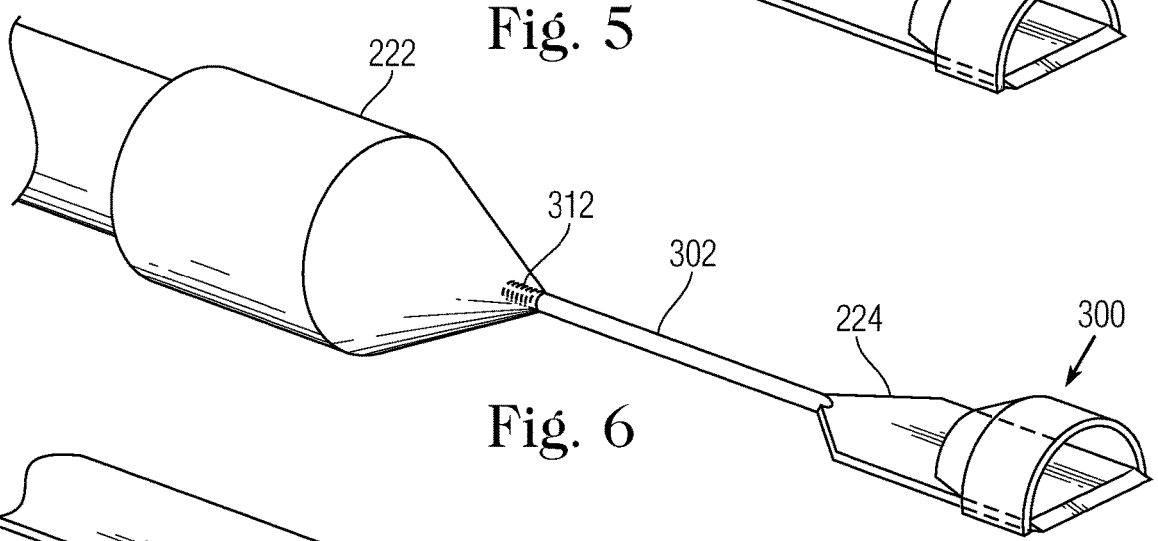
FIG. 6 is a perspective view of the connecting piece attached to a rod leading to the knife blade, which has a half conical structure at its distal end according to the third embodiment of the present invention.
Figure 9:
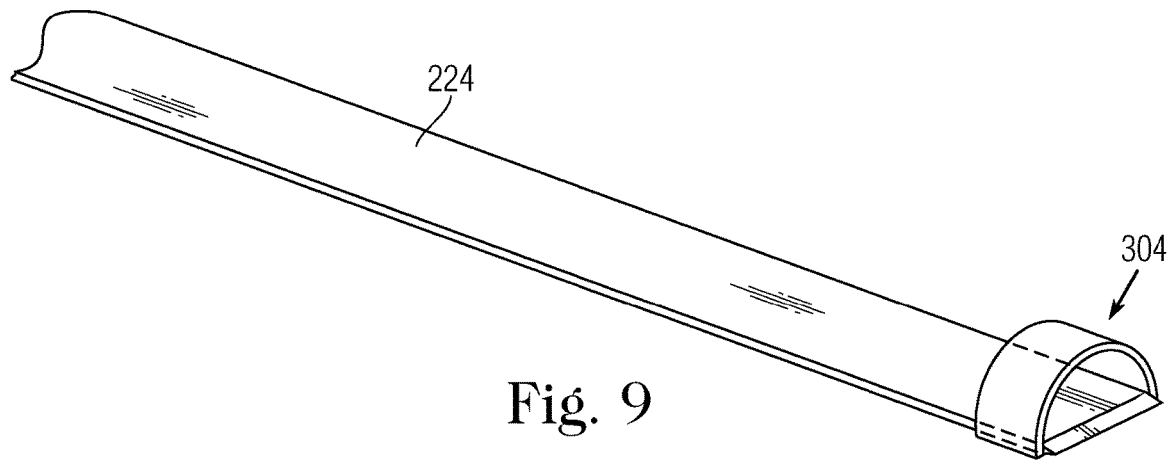
FIG. 9 a perspective view of a knife blade having a half ring structure at its distal end, but without showing a connecting piece according to the third embodiment of the present invention.
Figure 10:
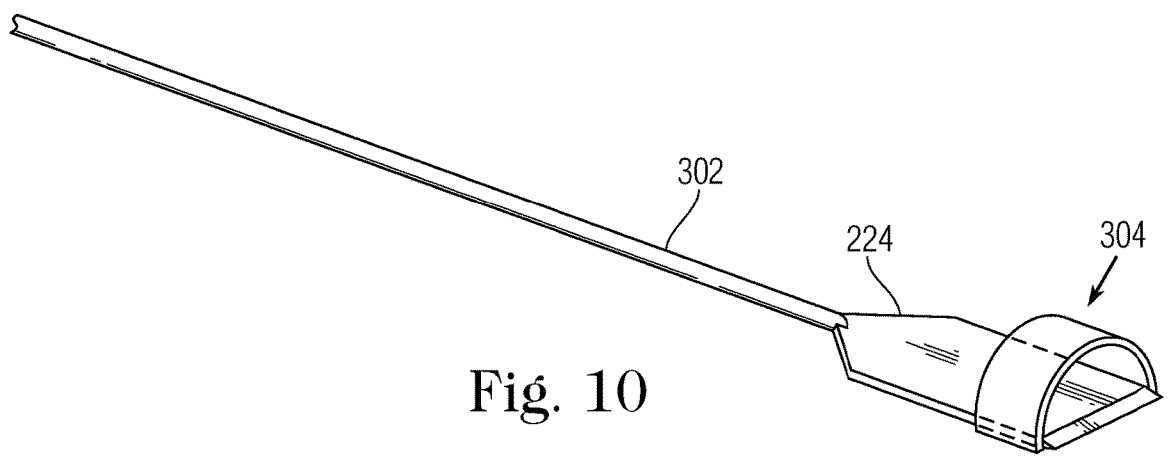
FIG. 10 is a perspective view of a rod attached to a knife blade that has a half ring structure at its distal end, but without showing a connecting piece according to the third embodiment of the present invention.
Figure 11:
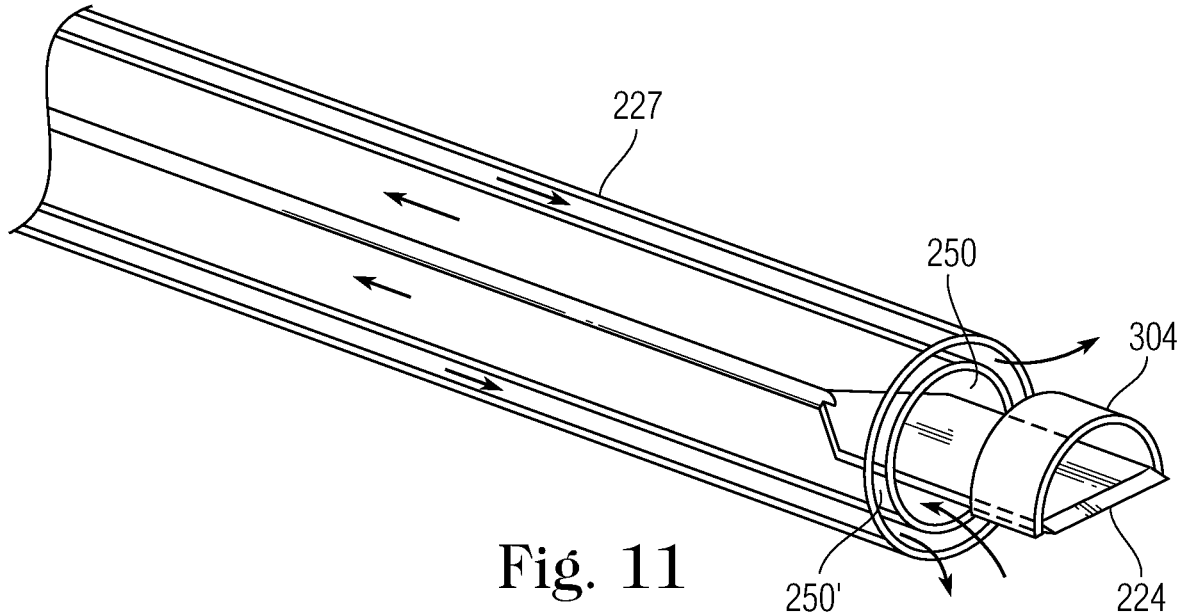
FIG. 11 is a perspective view of the distal end of a sleeve with irrigation and aspiration channels surrounding a rod with a knife blade at its end having a half ring according to a fourth embodiment of the present invention.

The double wall sleeve 227 of FIGS. 2 and 3 or the single wall sleeve 227' of FIGS. 4A-4C is designed to be used with one of the knives shown in FIGS. 5-10, as shown, for example in FIG. 11. FIG. 5, which is a third embodiment of the invention, shows a connecting body or hub 222 with a knife 224 extending from it. At the distal end of the knife there is a half Cobra tip 300, i.e., a cylindrical body with a conical shape at its proximal end. FIG. 6 shows the connecting body or hub 222 and a rod 302 extending form it to a portion of a knife 224. The connecting body and the rod are fixed to each other by a threaded connection 312. The distal end of the knife has half Cobra tip 300 fastened to it. The rod and connecting body or hub may be formed as one piece to lower the cost of machining the part. As an alternative the rod and/or blade may screw into the connecting body.

Figure 7:
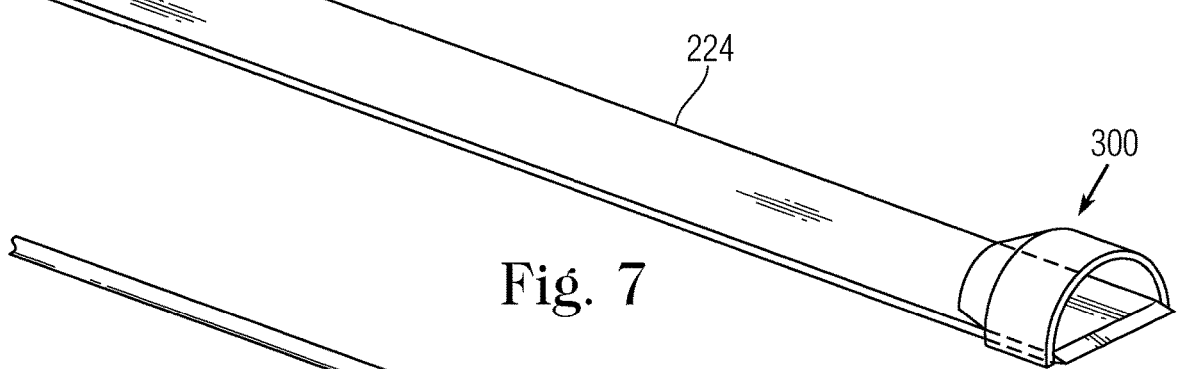
FIG. 7 is a perspective view of a knife blade having a half conical structure at its distal end, but without showing a connecting piece according to the third embodiment of the present invention.
Figure 8:
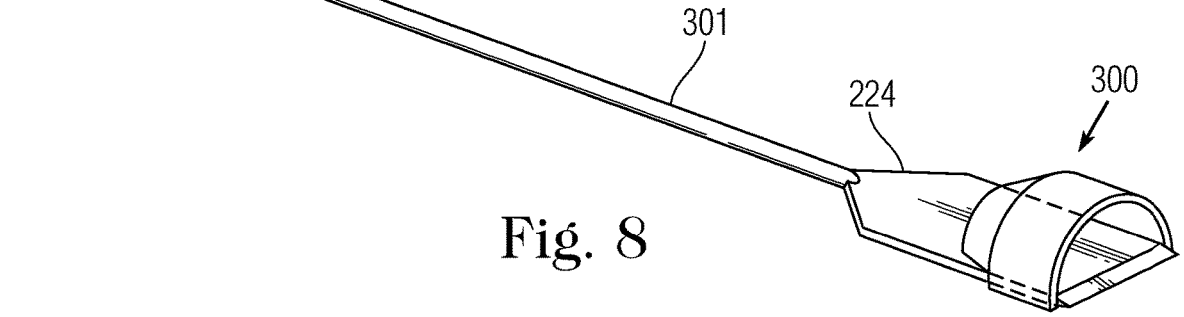
FIG. 8 is a perspective view of a rod attached to a knife blade that has a half conical structure at its distal end, but without showing a connecting piece according to the third embodiment of the present invention.

The design of FIG. 7 is similar to that of FIG. 5, but without the connecting body or hub. The design of FIG. 8 is similar to that of FIG. 6, but without the connecting body or hub. In FIG. 9 the design is like that of FIG. 7, but the half Cobra 300 is replaced with a half ring (collar) 304. In like fashion, the design of FIG. 10 is similar to that of FIG. 8, but with a half ring or collar 304.

In FIG. 11, which represents a fourth embodiment of the invention, the knife 224 of FIG. 10 is shown installed in the double-walled sleeve 227 of FIG. 3. The knife is vibrated at ultrasonic frequencies to break up the cataract. During this process irrigation fluid is directed to the surgical site through channel 250'. The emulsified tissue is withdrawn though channel 250, which also contains the knife. Note that the distal end of the knife has a shape edge for breaking the cataract. In addition, the distal edge of the collar 304 also impacts the cataract and assists in phacoemulsification.

Figure 12:
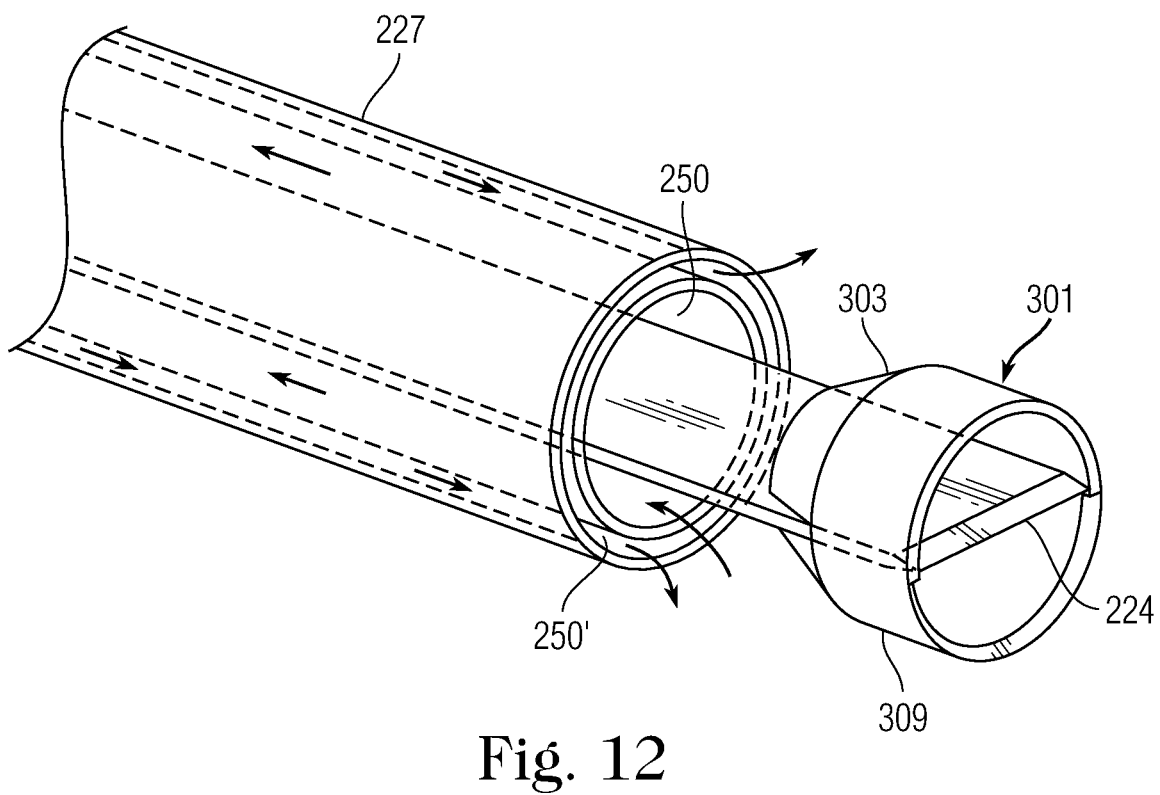
FIG. 12 is a perspective view of the distal end of a sleeve with irrigation and aspiration channels surrounding a knife blade with a full conical structure at its end according to the fourth embodiment of the present invention.

The arrangement of FIG. 12 has knife 224 with a full Cobra tip 301 at its distal end. This knife is positioned in the sleeve 227 of FIG. 3. Generally, the design of FIG. 12 operates similar to that of FIG. 11. However, the full Cobra tip 301 increases the force generated by the ultrasonic vibrations. In particular, the conical shape 303 of the Cobra tip causes fluid to be pushed toward the surgical site. Also, note that in FIG. 11, aspiration fluid can be drawn into channel 250 both above and below the knife, and in particular under the ring 304. In the design of FIG. 12 if the cylindrical part 309 of the Cobra tip 301 has a diameter similar to the diameter of channel 250', no or at least a limited amount of irrigation fluid can pass from this channel, but aspiration fluid can flow though the full Cobra tip to enters the channel 250 after the tip. Since irrigation is important, the diameter should not be made large enough to limit irrigation flow In the fifth embodiment shown in FIG. 13 there is the same knife as in FIG. 12, but the sleeve 227' is a single wall sleeve like that shown in FIGS. 4A-4C. The upper surface of the knife 224 slides under the bottom surface of the structure 306, which is in the distal end of sleeve 227'. The knife has a full Cobra tip 301 at its end. The conical wall 303 of the full Cobra tip forms an opening at the proximal end of the tip. The shape of this opening matches the shape of the structure 306 so that when the knife is withdrawn into the sleeve as shown in FIG. 14, the structure 306 blocks the portion of the opening at the proximal end of the tip that is located above the knife. The part of that opening below the blade is not blocked. As a result, irrigation fluid in the channel 250B can flow to the surgical site both when the knife is extended and when it is retracted.

Figure 13:
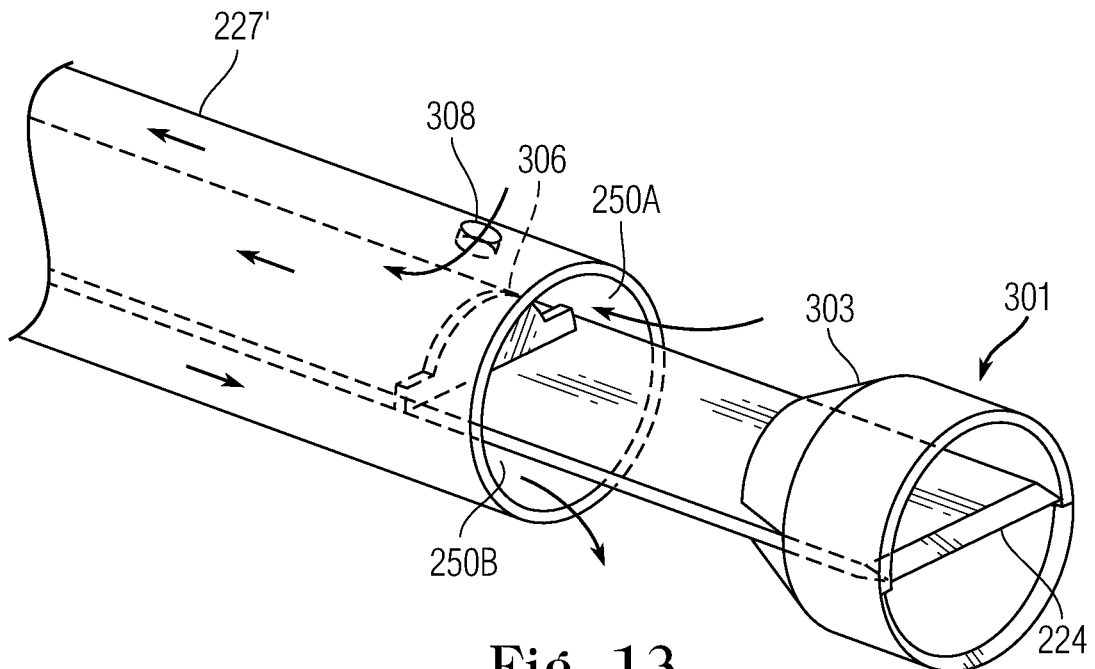
FIG. 13 is a perspective view of the distal end of a sleeve surrounding a knife blade in an extended state, a full conical structure at the end of the knife and a structure in the sleeve for changing the operation of the work tip according to a fifth embodiment of the present invention.
Figure 14:
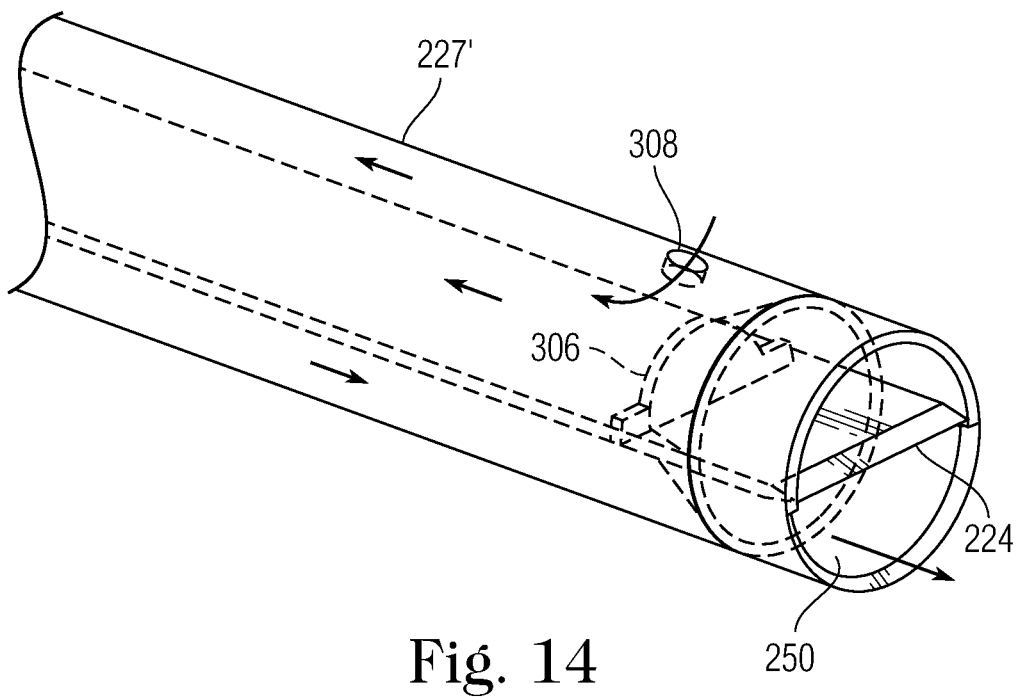
FIG. 14 is a perspective view of the arrangement of FIG. 13 with the knife in a retracted position.

The design shown in FIG. 13 with the knife extended is what is used for phacoemulsification. Aspiration fluid is withdrawn from the surgical site around and through the tip 301 and into the channel 250A above the knife. Also, a small amount of aspiration fluid flows through hole 308. When the tip is used for cleanup, the knife 224 is withdrawn into the sleeve 227'. The aspiration flow over the top of knife 224 and into chamber 250A becomes blocked by the structure 306, so the only path for aspiration is the reduced path through hole 308. Irrigation flow, however, can continue to flow through channel 250B.

Figure 15:
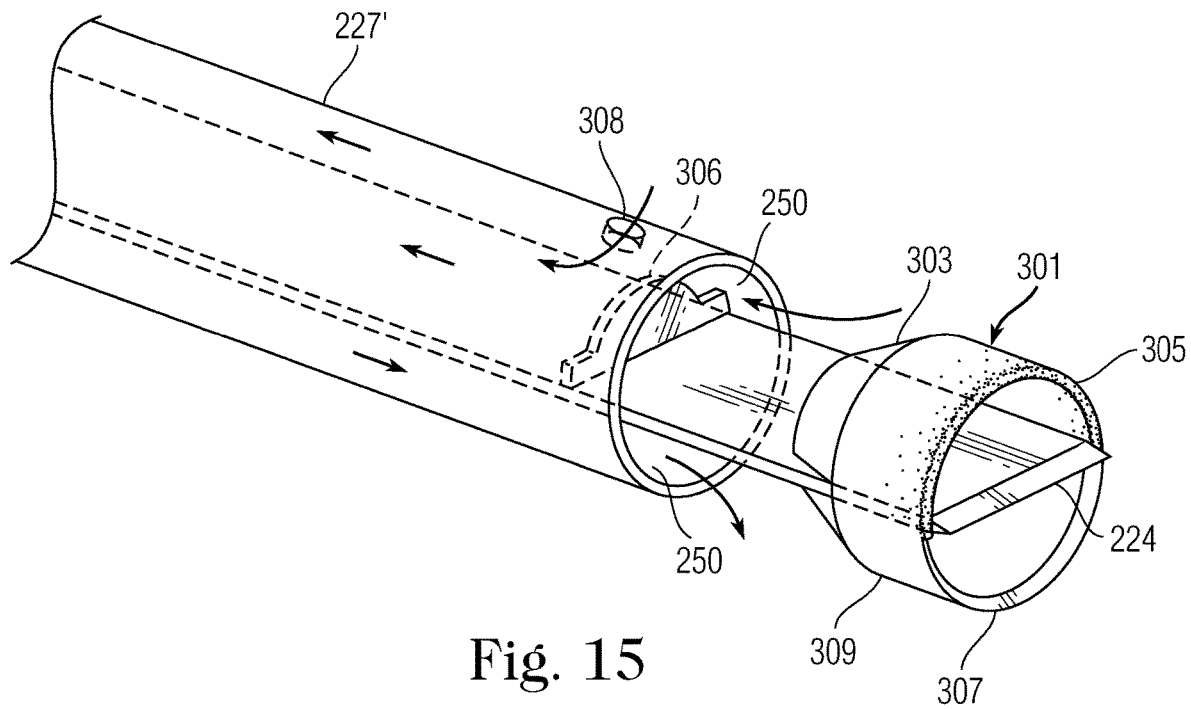
FIG. 15 is a perspective view of the arrangement of FIG. 13, but with an upper portion of the distal end of conical shape having a rounded textured surface and the lower portion being in the form of a sharp cutting edge.

FIG. 15 shows the same arrangement as FIG. 13, but an upper portion 305 of the distal end of the conical shape has a rounded textured surface and the lower portion 307 is in the form of a sharp cutting edge. The texturing of surface 305 can be achieved by several methods, for example by sand blasting. This textured surface is used to scrape the epithelial cells form the posterior capsule during the I/A procedure. The bottom half of the work tip with the sharp edge is used to cut the cataract.

Figure 16:
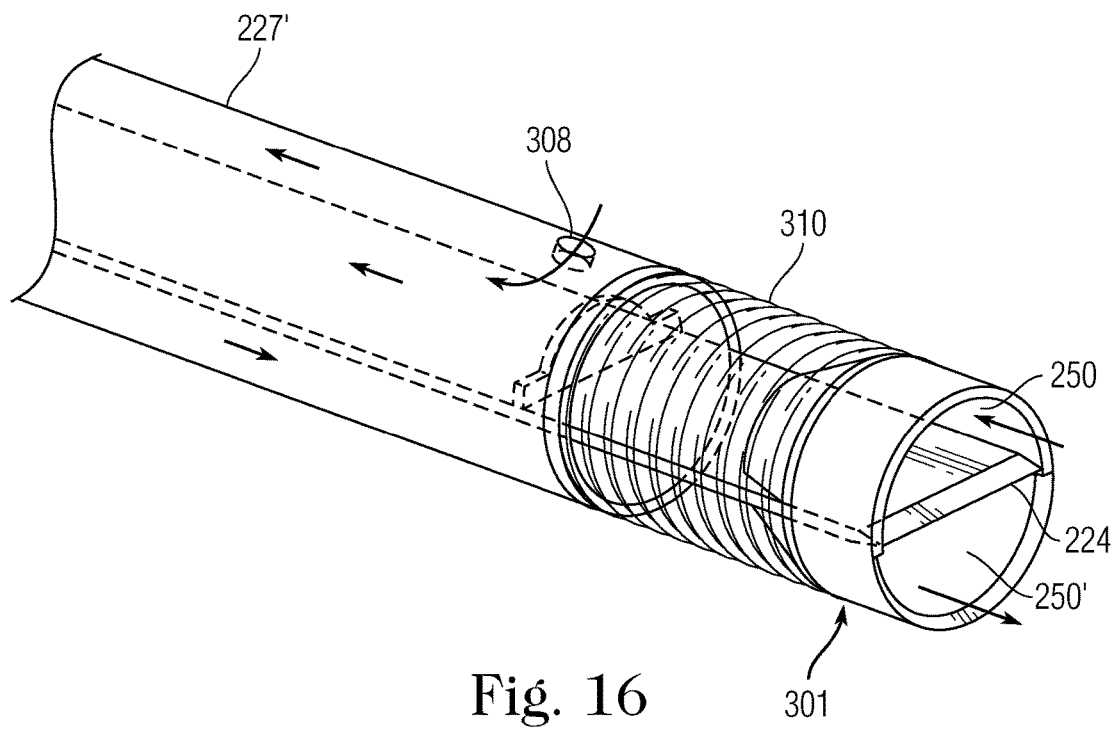
FIG. 16 is a perspective view of the arrangement of FIG. 13 further including a protective sheath between the distal end of the sleeve and the expanded part of the conical shape.

FIG. 16 shows the same perspective view of the work tip as shown in FIG. 13; but, equipped with a protective sheath 310 provided between the distal end of the sleeve 227' and the expanded or cylindrical part 309 of the conical/Cobra shape 301. Because of the sheath 310 fluid cannot flow around the Cobra tip but must go through the Cobra tip. The sheath can be thin, flexible and transparent.

Figures 17A, 17B:
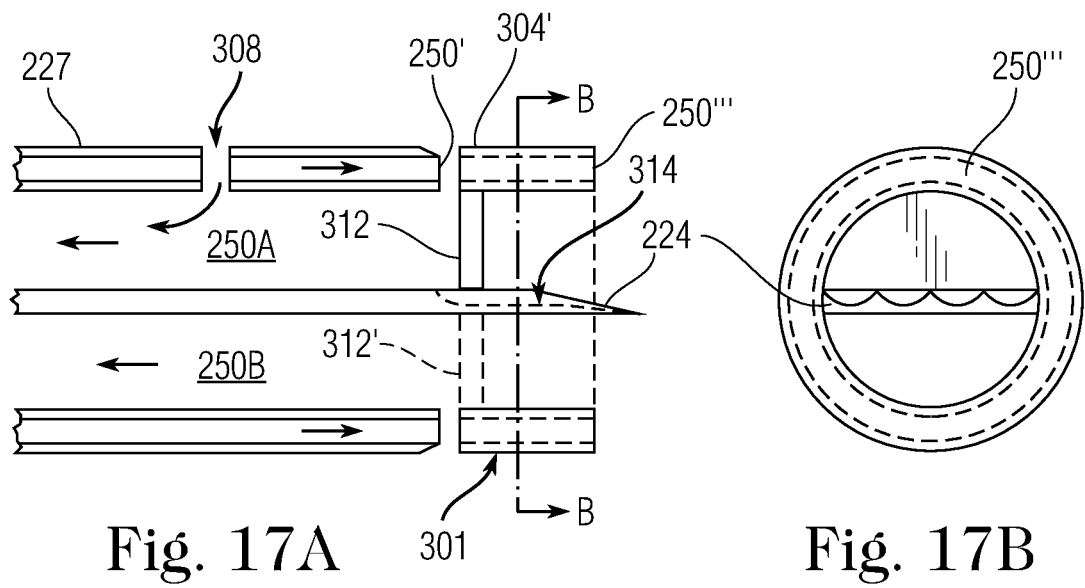
FIG. 17A is a side view of an arrangement similar to FIG. 11 but with a full ring and showing the blade surrounded by a sleeve with fluid irrigation channels and a radial blocking structure in the tip.
FIG. 17B is a front cross-sectional view along line B-B of the structure of FIG. 17A with the structure in the tip blocking the upper channel.

A side view of the arrangement of FIG. 11 with a collar 304 at the work tip is shown in FIG. 17A. A front cross-sectional view of this arrangement is shown in FIG. 17B. Unlike the structure of FIG. 11, in FIG. 17A the collar 304 extends completely around the knife 224, i.e., it is full collar 304'. Further, like the arrangement in FIG. 15, there is a structure 312 that blocks the channel 250A above the knife when the knife is retracted into the sleeve 227. However, the structure 312 is located at the proximal end of the collar and not within the sleeve. When the knife is extended, and a phacoemulsification operation is begun, the ultrasonic vibration of the collar breaks up the cataract. In addition, the vibration of wall 312 causes fluid cavitation that assists in breaking up the cataract. This perpendicular wall 312 is even more efficient in this respect than the conical wall 303 of a standard Cobra tip. The irrigation flow is in channel 250' during phacoemulsification and aspiration can be through channels 250A and 250B. During clean up, depending on the structure of collar 304', it can either block irrigation flow when the knife is fully retracted, or the collar can be provided with an extension of the channel 250''' so that irrigation fluid continues to reach the surgical site during clean up when the knife is retracted into the sleeve. In the fully retracted position the wall 312 blocks aspiration channel 250A, which tends to cause more aspiration to occur through hole 308, which can be ideal for cleanup. A similar wall 312' shown in dotted line can be provided on the tip 304' below the knife so as to block channel 250B and cause all of the aspiration to occur through hole 308.

Figure 18:
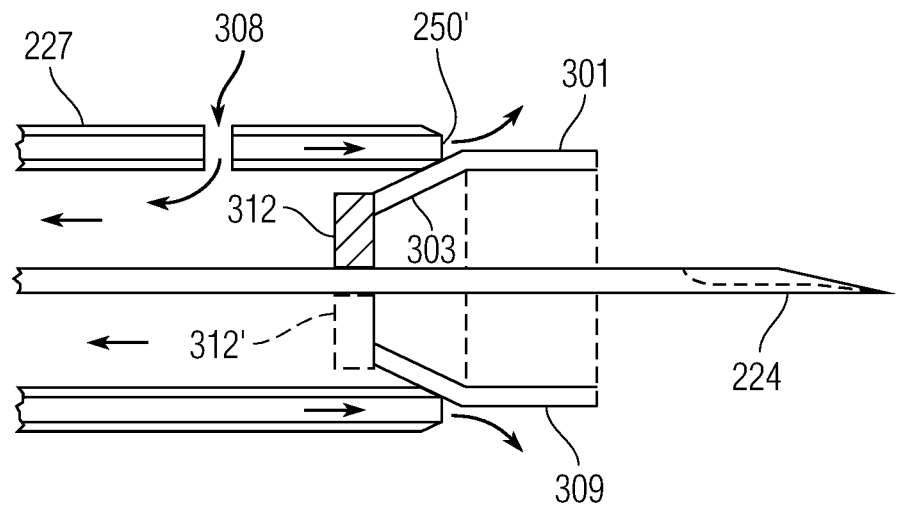
FIG. 18 is a side view of the structure similar to that of FIGS. 13 and 14 showing the blade and a structure within the sleeve blocking the proximal end of the cone shape.

FIG. 18 shows a side view of a schematic arrangement like that in FIG. 17A, but with a Cobra tip 301 instead of the collar 304. FIG. 18 shows the knife in the retracted position in which the opening at the proximal end of the conical surface 303 is blocked by the structure 312. As an option in this arrangement as well as in the arrangement of FIG. 17A, the cylindrical portion of the tip is smaller in diameter than the channel 250' so that even in the retracted position irrigation fluid can flow from channel 250'.

Figure 19:
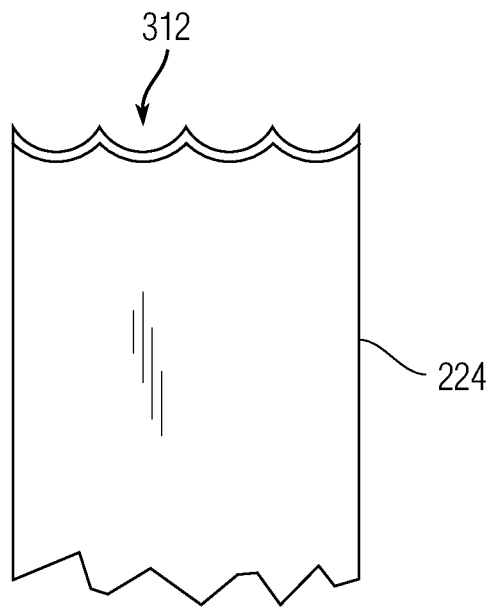
FIG. 19 is a plan view of a knife according to the present invention with a serrated edge.
Figure 20A:
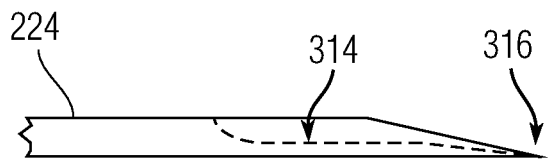
FIGS. 20A and 20B are side and plan views of a knife according to the present invention with scalloped edges.
Figure 20B:
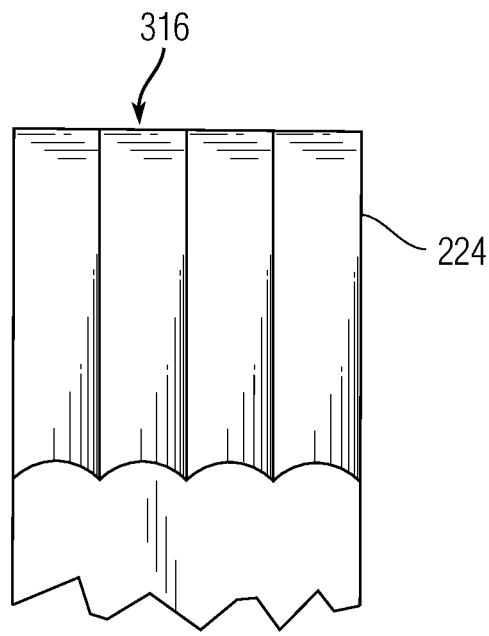

The end of the knife 224 in FIG. 18 shows a scooped portion in dotted line that is shown in side view in FIG. 20A and plan view in FIG. 20B. FIG. 19 is a plan view of the knife 224 with a serrated edge. This shape helps in the cutting of the cataract. As indicated FIGS. 20A and 20B are side and plan views of the knife 224 with scalloped edges. These edges also help with cutting of the cataract.

Figure 21A:
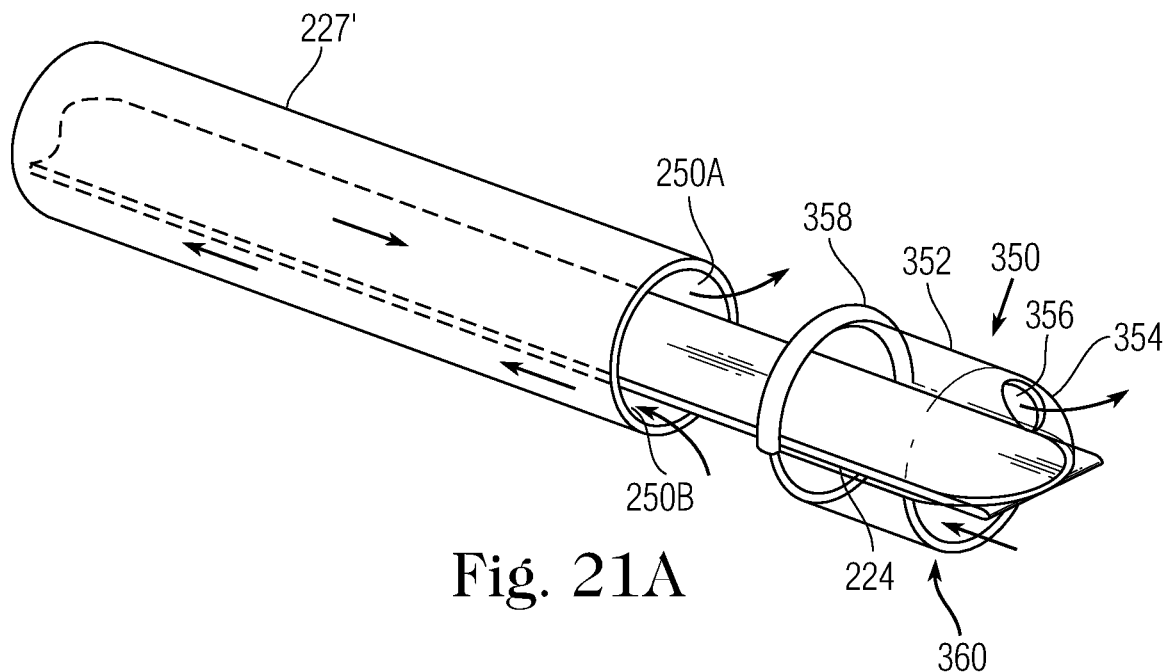
FIG. 21A is a perspective view of a sixth embodiment with a work tip in the form of a half cylindrical/hemispherical structure on top of a blade and a collar below the blade, with the work tip in an extended position with regard to a sleeve.
Figure 21B:
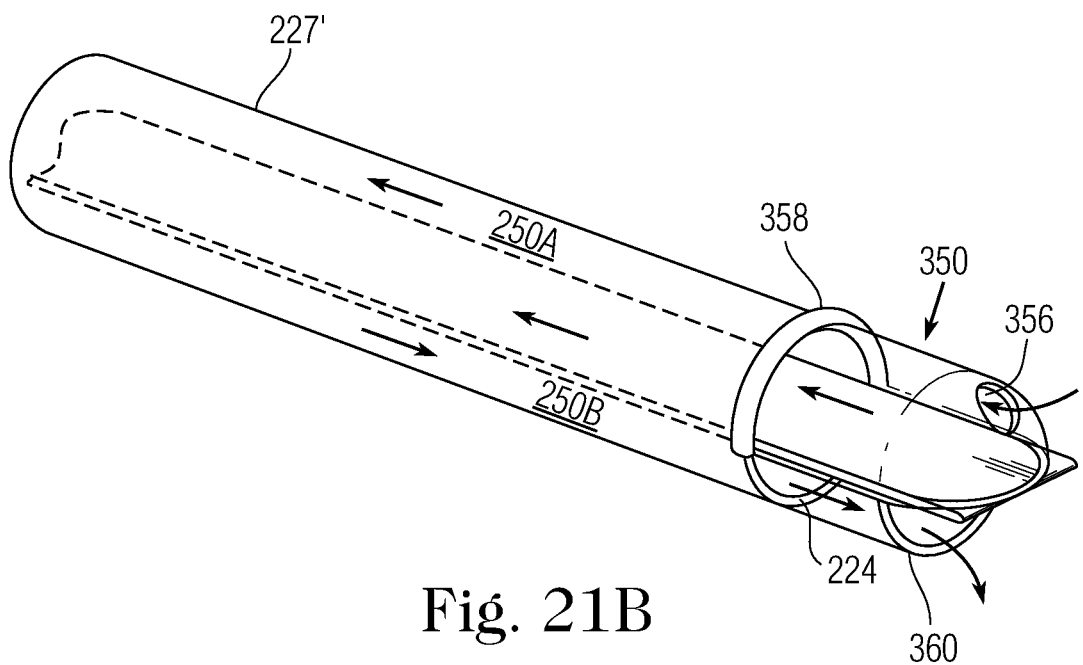
FIG. 21B is a perspective view of the embodiment of FIG. 21A in the retracted position.

FIGS. 21A and 21B show a sixth embodiment of the present invention with a work tip in the form of blade 224 that has a half cylindrical/hemispherical structure 350 on the upper surface of the blade. A half collar 360 is located on the lower surface of the blade at about the location of the half cylindrical/hemispherical structure 350. The structure 350 includes a half cylindrical part 352 and a half hemispherical part 354 that is on the distal end of the part 352. The part 354 has an aspiration hole 356. The proximal portion of the half cylindrical part 352 has a sealing member 358. During phacoemulsification, it is the distal edge of the collar 360 that scoops out or cuts the cataract. During cleanup, the instrument is turned over so only the smooth surface with the aspiration opening 356 that contacts the ocular sack.

The position shown in FIG. 21A has the work tip extended from the single walled sleeve 227'. If additional fluid flow arrangements were of interest, sleeve 227' could be replaced with a double walled sleeve 227 where fluid flow would exist between the walls as shown in FIG. 3. The embodiment of FIG. 21 is used for phacoemulsification when in the extended position of FIG. 21A. The portion of collar 360 below the blade 224 engages a cataract (not shown) while being vibrated at an ultrasonic frequency. This causes the cataract to break up into small pieces. During this time irrigation fluid passes through the sleeve from the hand piece (not shown) in the space 250A above the blade 224. It can exit the space between the distal end of the sleeve 227' and the structure 350, and flow around that structure to the surgical site. A portion of the irrigation fluid can also pass through hole 356 in structure 350 to the surgical site.

During phacoemulsification, the small pieces of cataract are aspirated by fluid flow into the sleeve through the space 250B. Pieces are drawn directly from the surgical site through the collar 360 and into the space 250B. In addition, some fluid is drawn from the space between the half cylindrical/hemispherical structure 350 and the distal end of the sleeve.

When it is time for irrigation/aspiration (I/A) cleanup of remaining epithelial cells on the capsular sack, the ultrasonic vibration may be reduced or turned off. Also, the work tip is withdrawn so that seal 358 engages the distal end of the sleeve above the blade as shown in FIG. 21B and closes off the flow of fluid above the blade and between the sleeve and work tip. In this state the fluid flow is reversed so that aspiration flow is set up in channel 250A. Thus, at the surgical site, aspiration occurs only through hole 356 on the rounded surface 354. This is much like a separate conventional I/A tool, but is part of a phacoemulsification tool, so 2 in 1 functionality is provided. During this I/A procedure, irrigation fluid is passed through channel 250B of the sleeve 227' below the blade 224, and through the collar 360 to the site of the cleanup.

The reversal of fluid flow can be by way of valves in the hand piece or the control apparatus as is well known in the art.

The work tip of FIGS. 21A & B can be made of metal, for example titanium. As an alternative, the half cylindrical/hemispherical structure 350 could be made of hard plastic or even some composite material that will withstand ultrasonic vibration, while the seal 358 is made of an elastomeric material.

Figure 22A:
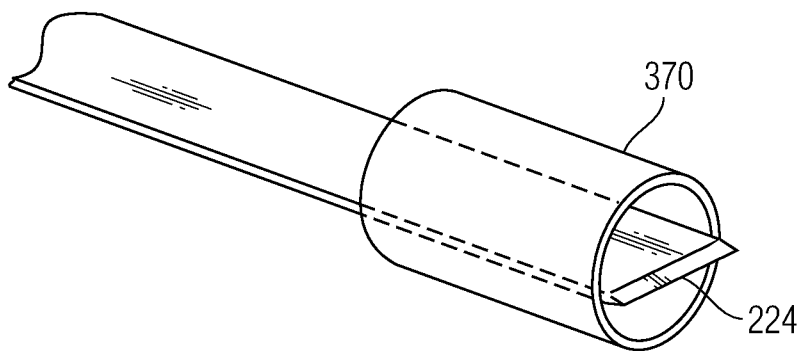
FIG. 22A shows a work tip with a full collar surrounding a blade.
Figure 22B:
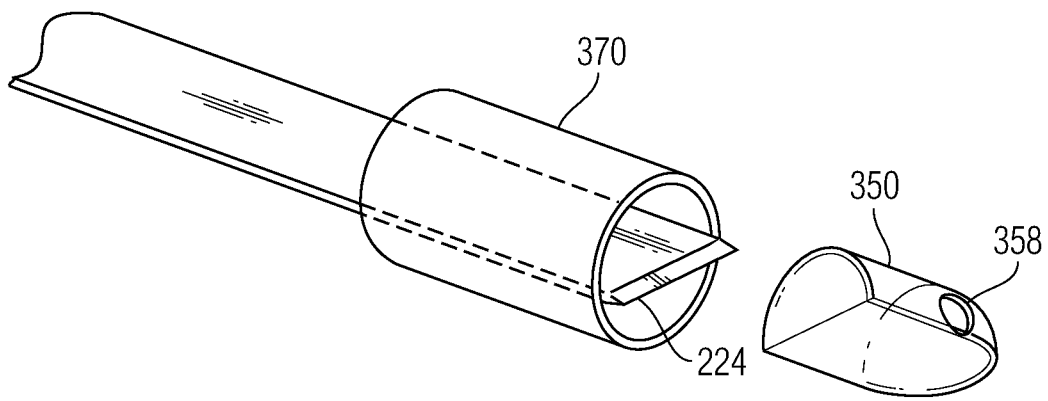
FIG. 22B shows a half cylindrical/hemispherical insert that fits in the collar of the work tip of FIG. 22A above the blade.
Figure 22C:
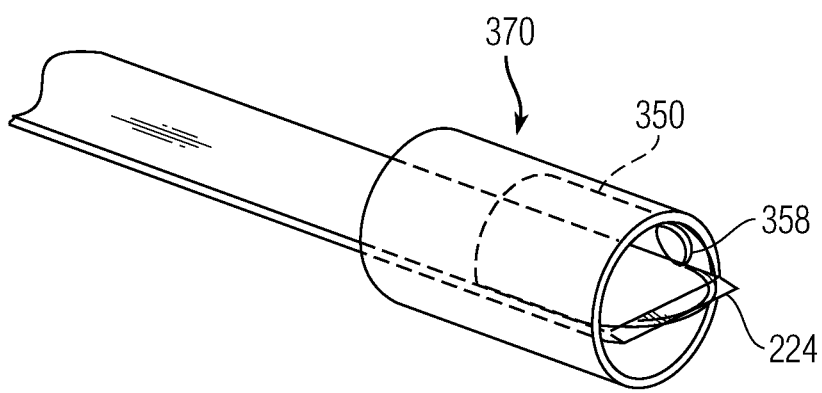
FIG. 22C shows the insert in position in the collar for operation according to the embodiments of FIG. 21.

FIG. 22A shows a work tip with a full collar 370 surrounding a blade 224. FIG. 22B shows the half cylindrical/hemispherical structure as a separate insert 350. This insert is adapted to fit in the collar 370 and be attached to the upper surface of the blade 224. FIG. 22C shows the insert 350 in position in the collar 370. When assembled in this way, the work tip of FIG. 22C can be operated similar to the embodiments of FIG. 21 discussed above.

Figure 23A:
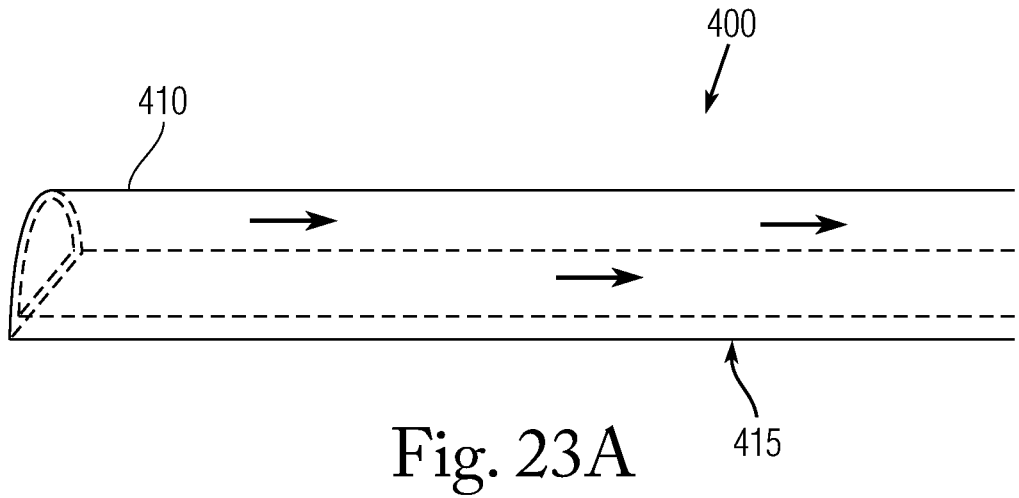
FIGS. 23A-C form an exploded perspective view of a seventh embodiment of a work tip according to the present invention with a top tube (FIG. 23A), a blade (FIG. 23B) and a bottom tube (FIG. 23C), which embodiment can be changed from phacoemulsification to A/I clean up by sliding the blade with respect to the bottom tube.
Figure 23B:
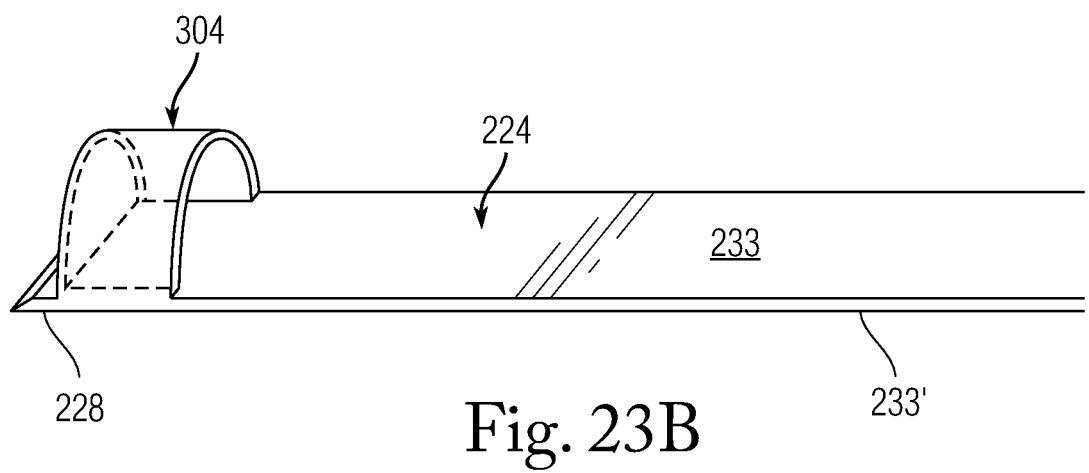
Figure 23C:
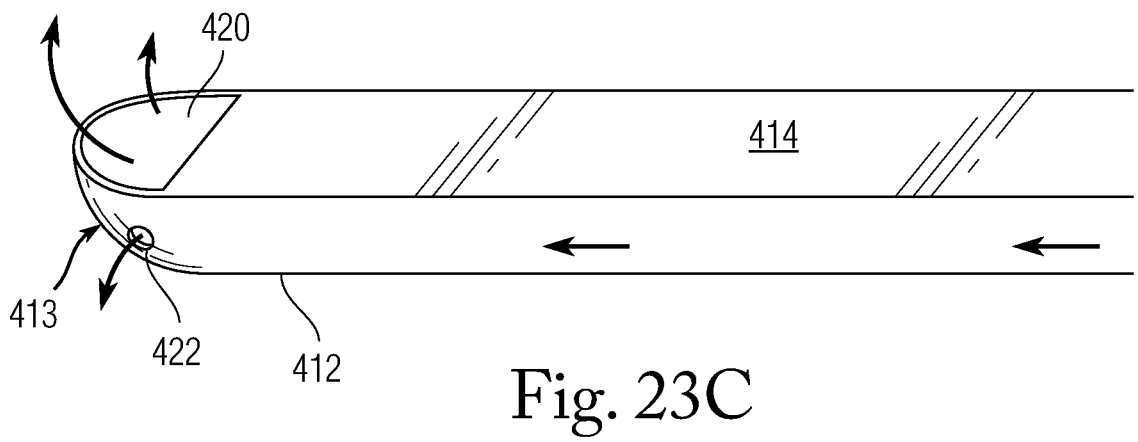

A work tip 400 according to a seventh embodiment of the present invention is shown in FIGS. 23A-C. It includes a top fluid tube 410 in FIG. 23A, which during phacoemulsification acts as an aspiration tube. In this embodiment the tube is in the form of a half cylinder open at both ends. The bottom 415 of tube 410 is generally flat and the opposite surface has a cylindrical shape. Also, this embodiment includes a knife blade 224 (FIG. 23B) with a sharp edge 228 at its most distal end and opposing top and bottom surfaces 233, 233'. A half ring structure 304 extends from surface 233 at its distal end, like that in FIG. 9.

A bottom tube 412 (FIG. 23C) is provided below the knife blade 224. The bottom tube 412 has a half cylinder shape over most of its extent but has a half hemispherical shape 413 at its most distal end. During phacoemulsification this tube acts as an irrigation tube. Irrigation fluid exits the distal end of the tube 412 through a half circular opening 420 in its upper most surface 414 in the area of the half hemispherical shape 413 and through a hole 422 in a side of the half hemispherical shape 413. In the practice of the present invention the upper and lower tubes can have shapes other than the half cylindrical shapes shown, e.g., square or circular shapes are permissible. Also, as will be shown, the knife can also have other shapes.

It should be noted that throughout this specification when directions are noted such as "top" and "bottom," these are relative terms referring to the structure as shown in the drawings. Thus, if the work tip is turned over, the top and bottom with respect to a gravitational field would change, but the relative positions of the parts remain the same.

When the three components of the embodiment are assembled, they result in the structure shown in FIG. 25A in which the bottom surface 415 of the upper tube 410 is located on the top surface 233 of the knife 224 proximally of the ring structure 304, and the top surface 414 of the bottom tube 412 is located adjacent the bottom surface 233' of the knife. With this arrangement, during phacoemulsification, the blade 224 is vibrated, perhaps at an ultrasonic frequency or higher or lower. The edge 228 of the blade and the distal side of the half ring structure 304 act to break up cataract tissue. During this operation irrigation fluid is provided to the operating site from bottom tube 412 through opening 420 and hole 422. At the same time, pieces of tissue are aspirated by the withdrawal of fluid from the operating site through tube 410 as shown by the arrows in FIG. 25A. FIG. 25B shows a top view of the work tip 400 structure with the tube 410 removed for the sake of clarity.

Figure 24A:
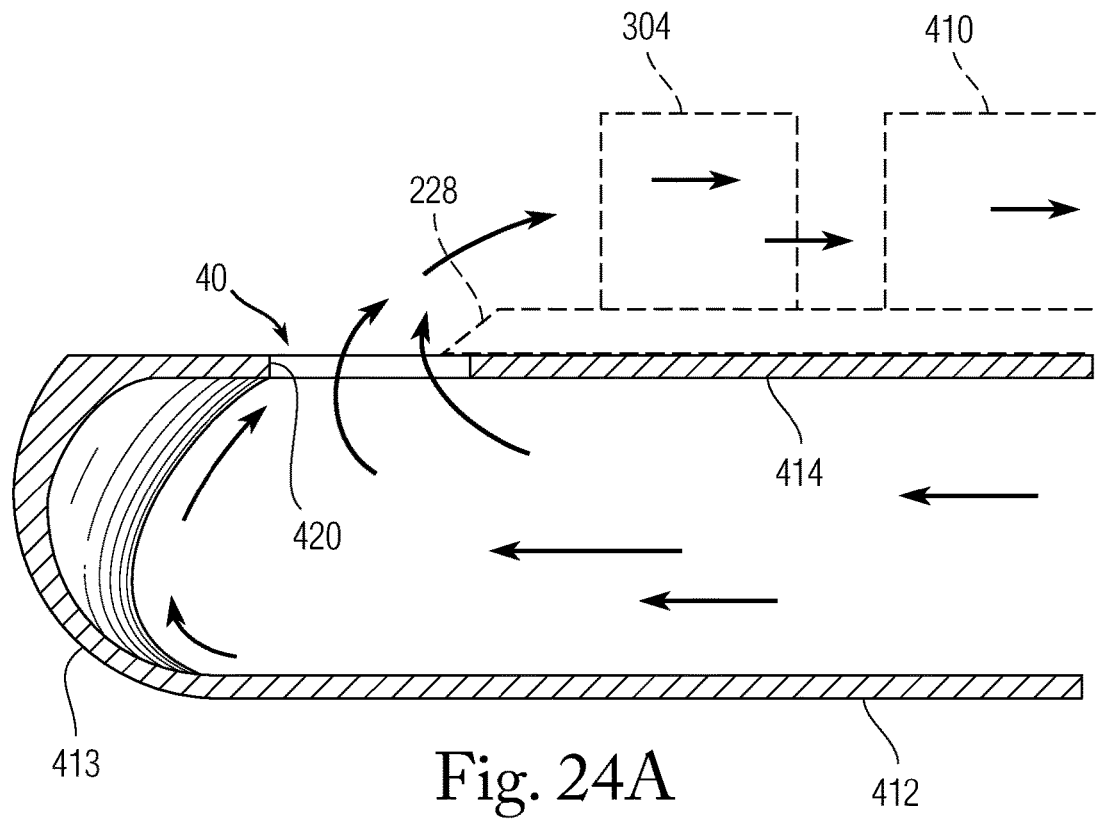
FIG. 24A is a side view of the bottom tube showing grooves or baffles for directing irrigation fluid flow during phacoemulsification.
Figure 24B:
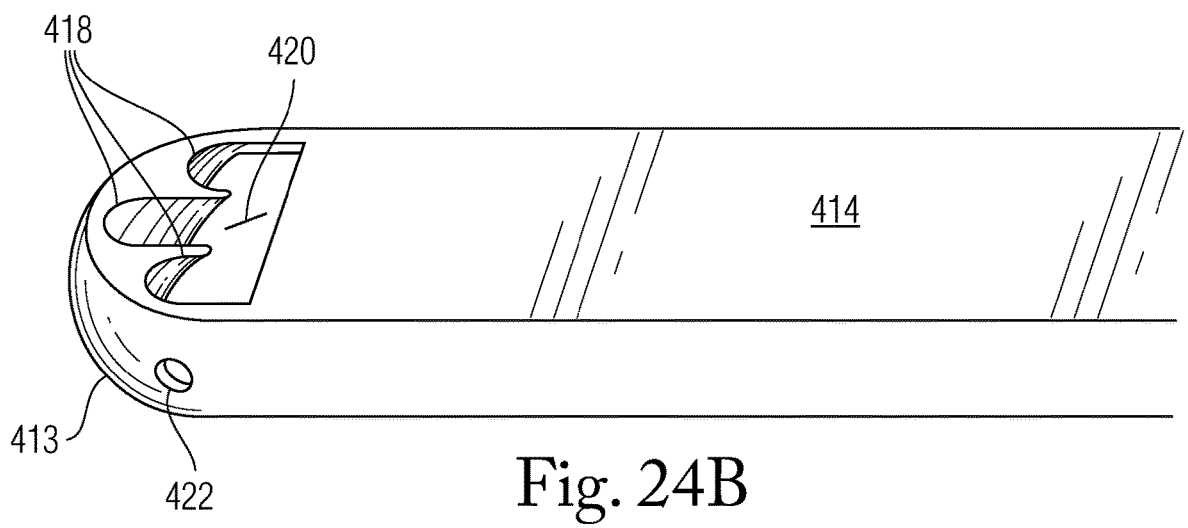
FIG. 24B is a top view showing the grooves or baffles.

The irrigation fluid flowing through opening 420 and the vibration of blade 224 and half ring structure 304 can disrupt the flow of issue into aspiration tube 410. It is proposed to modify this flow to bring about better removal of the tissue. This can be accomplished by providing grooves or baffles 418 in the half hemispherical portion 413 of the bottom tube as shown in FIG. 24A and FIG. 24B, where the aspiration tube 410 and knife blade with cutting edge 228 are shown in dotted line in FIG. 24A and have been removed in FIG. 24B for the sake of clarity. For example, as shown in FIG. 24A the grooves 418 tend to direct the irrigation fluid back toward the aspiration tube 410. This creates a laminar fluid flow from opening 420 to the entrance to tube 410. Note that this flow will be through the focus of the vibrational energy on the cataract tissue at cutting edge 228 so that tissue pieces are efficiently entrained in the stream.

By comparing FIG. 25A and FIG. 25C, it can be seen that the knife blade 224 can be moved with respect to the bottom tube 412 or vice versa. When in the position shown in FIG. 25C the handpiece is useful for I/A clean up. During such an operation the vibration of the knife blade is stopped. Because the solid portion of knife blade 224 is slid over the opening or hole 420 in the bottom tube 412, it is closed off. If aspiration force is applied to bottom tube 412 at a reduced pressure, cleanup can be carried out by hole 422 in the half hemispherical portion 413 of the bottom tube. This surface is smooth and is remote from the cutting edge 228 and the edge of half ring or collar 304, so it is ideal for I/A.

During phacoemulsification with the structure of FIG. 25A, the sharp edge 228 of the knife is somewhat enclosed by the half hemispherical region 413 of the bottom tube. Thus, to effect contact with cataract tissue, it may need to be turned upside down from the position shown in that figure or otherwise manipulated. Even so, the distal edge of ring 304 is still effect for emulsifying tissue.

Figure 26A:
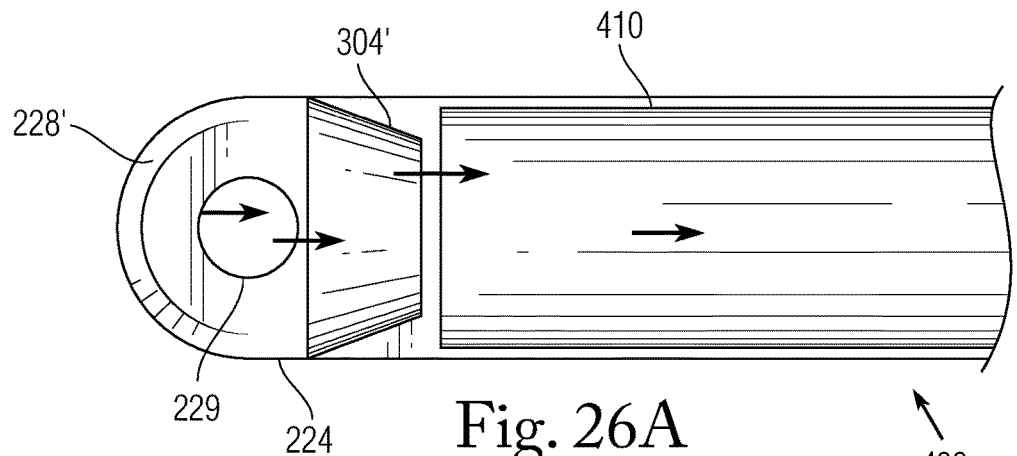
FIG. 26A is a top view of an eighth embodiment of the present invention with a conical sleeve toward the distal end of the blade.
Figure 26B:
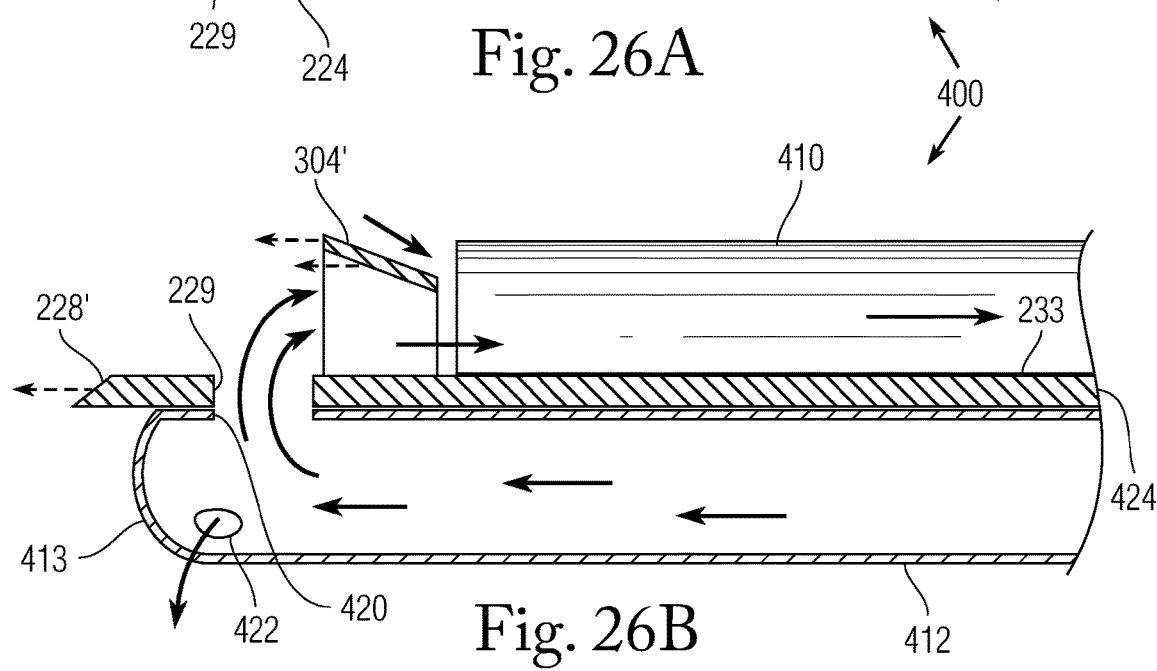
FIG. 26B is a cross-section of a side view of the embodiment of FIG. 26A with the blade in the extended position and FIG. 26C is a cross-section of a side view of the embodiment of FIG. 26A with the blade in the retracted position.
Figure 26C:
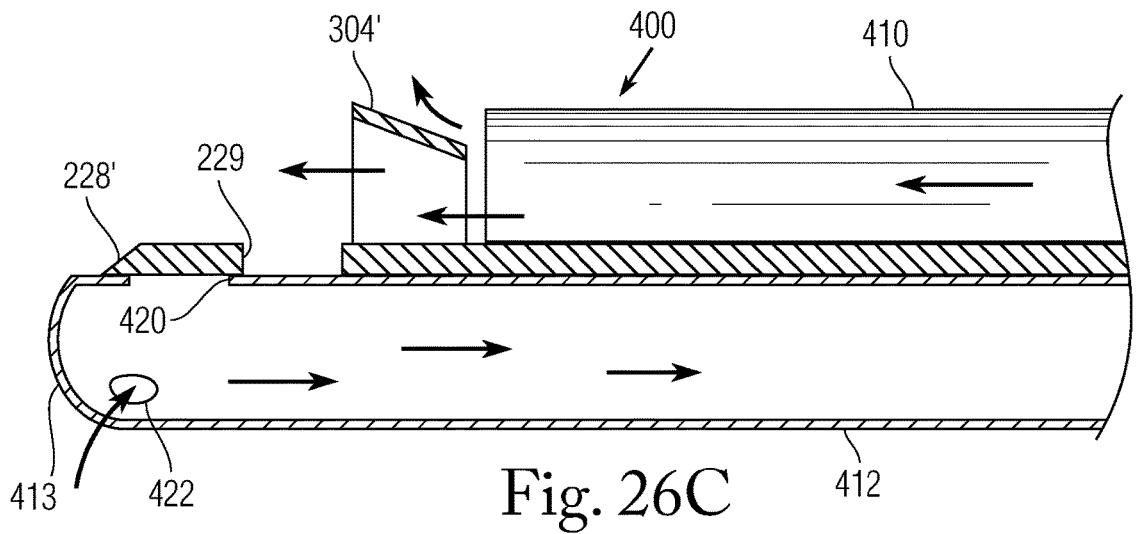

FIGS. 26A-C illustrate an eighth embodiment of the invention which allows for the cutting edge 228' of the knife to extend beyond the hemispherical region 413 of the bottom tube and better engage the cataract tissue. This embodiment includes the bottom tube 412, the top tube 410 and the knife blade 224. The knife blade includes a half ring or collar 304', which is like collar 304 of FIG. 25, except that it has a conical shape sloping downward from its distal edge to its proximal edge. The knife is also different in that it has a hole 229 in it that aligns with the hole 420 in the upper surface of tube 412. The outer edge of the knife 224 is a sharp curved cutting edge 228'.

When performing phacoemulsification, the work tip 400 is as shown in FIGS. 26A and 26B. In that mode the blade 224 is vibrated at some high frequency so that cutting edge 228' can contact and emulsify cataract tissue. Irrigation fluid is received in tube 412 passes through hole 420 in the top surface of the tube 412 and through aligned hole 229 in the blade. The flow after passing through the blade is toward the conically shaped collar 304'. Because of its shape the collar collects the fluid stream from tube 412 and directs it toward the top tube 410 for removal with the aspiration fluid. The shape of the collar not only acts to capture the irrigation flow and to better control it, its shape also acts like a Cobra work tip used at the aspiration lumen in order to affect a very efficient breakup of the cataract. This shape provides a very efficient transfer of ultrasonic or other vibration force to the cataract because, not only is the distal edge diameter expanded, but the slope of the internal surface generates and transmits additional sonic energy (small dotted arrows) to emulsify more of the cataract than a straight lumen. See U.S. Pat. No. 5,242,385 of Strukel, which is incorporated herein by reference in its entirety.

As shown in FIG. 26C, during I/A clean up, the vibration of the blade is slowed or stopped, and the fluid flow direction is reversed in tubes 410 and 412. Further by sliding the blade back with respect to tube 412 the hole 229 is no longer aligned with hole 420 in tube 412. As a result, holes 229 and 420 are closed. Thus, aspiration can only occur through hole 422 in the half hemispherical portion 413 of tube 412. Note that in this position the sharp edge 228 has been retracted and will not damage the surrounding tissue during cleanup. Irrigation fluid for cleanup is provided through tube 410.

Figure 27A:
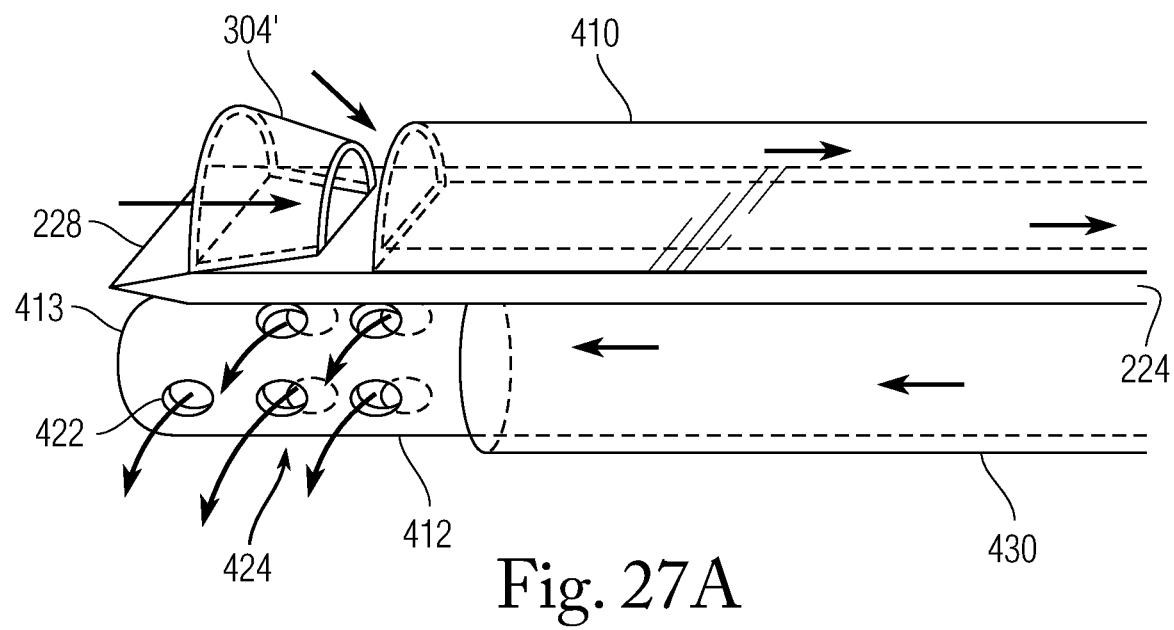
FIG. 27A is a perspective side view of a ninth embodiment of the present invention in which multiple holes are provided at the distal end of the bottom fluid tube and the work tip is set up to perform phacoemulsification and FIG. 27B is a view wherein a movable sleeve has been moved forward to cover most of the holes in the bottom fluid tube so the work tip can perform I/A cleanup.
Figure 27B:
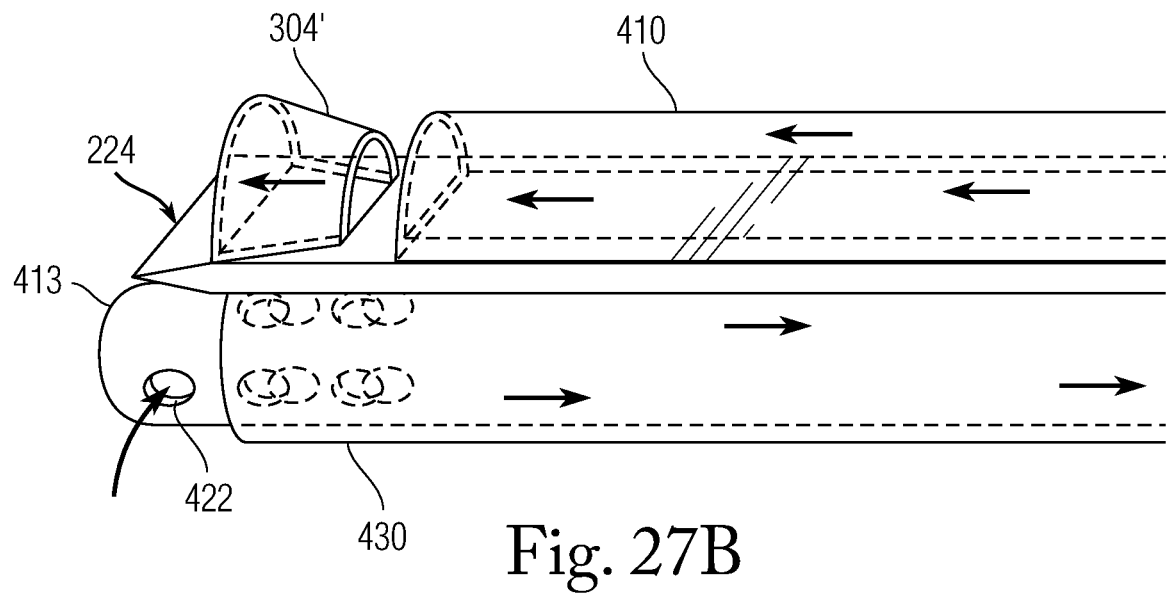

A ninth embodiment of the invention is shown in FIGS. 27A and 27B. In this embodiment the top tube 410 is the same as in the eight embodiment. The knife blade 224 has sharp edge 228 and the conical half ring or collar 304', but it does not have a hole. The bottom tube 412 has no hole in its upper surface, but it has a hole 422 in the half hemispherical section 413. Further, the bottom tube has a plurality of openings 424 in the cylindrical portion of tube 412. It also has a sleeve 430 that can be slid along tube 412.

During phacoemulsification as shown in FIG. 27A, tube 430 is withdraw so as to expose all of the holes/openings 422, 424 to provide irrigation to the surgical site. The knife blade 224 is vibrated so its cutting edge 228 can engage the cataract tissue. The conical shape of half ring 304' also enhances the emulsification of the cataract tissue by applying additional sonic energy. Further the distal edge of half 304' may be sharp enough to provide additional cutting. Aspiration is provided through conical collar 304' and tube 410.

During I/A cleanup, the vibration of the blade 224 is stopped, and the fluid flow direction is reversed in tubes 410 and 412. Further the openings 424 are blocked by sliding sleeve 430 forward to cover them as shown in FIG. 27B.

Figure 30A:
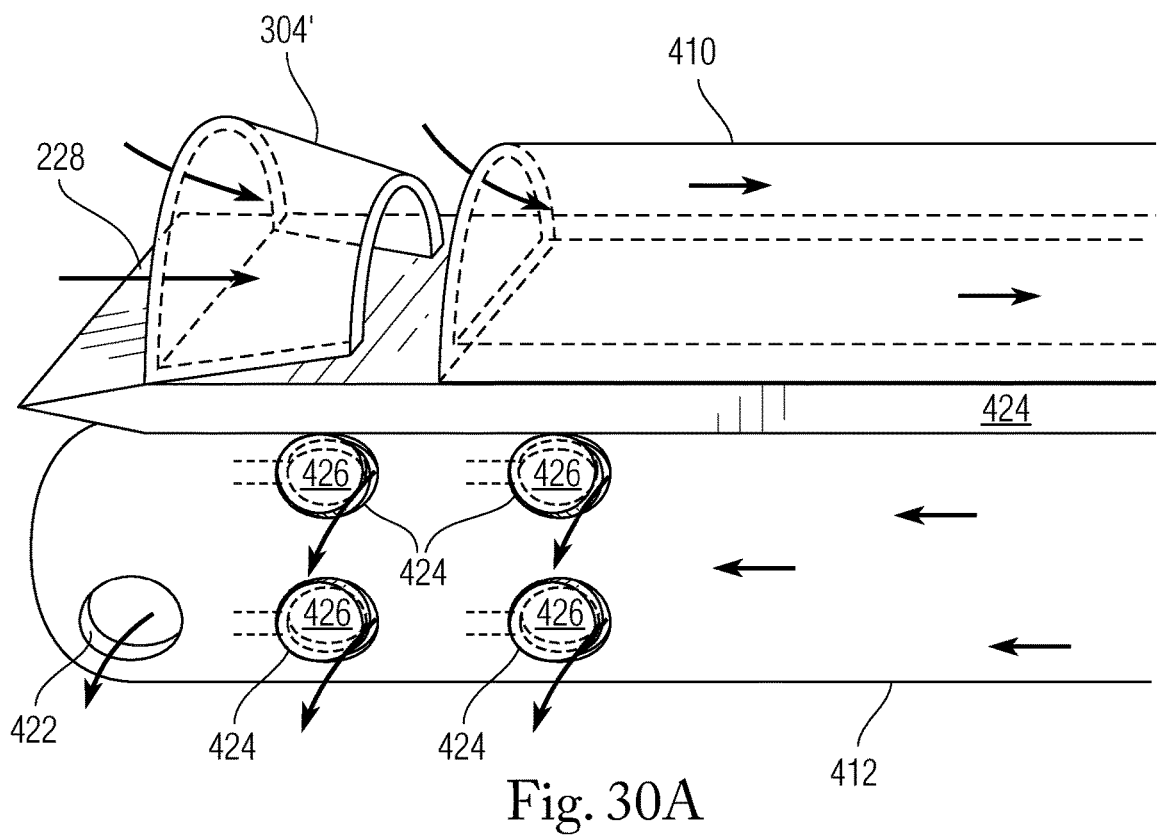
Figure 30B:
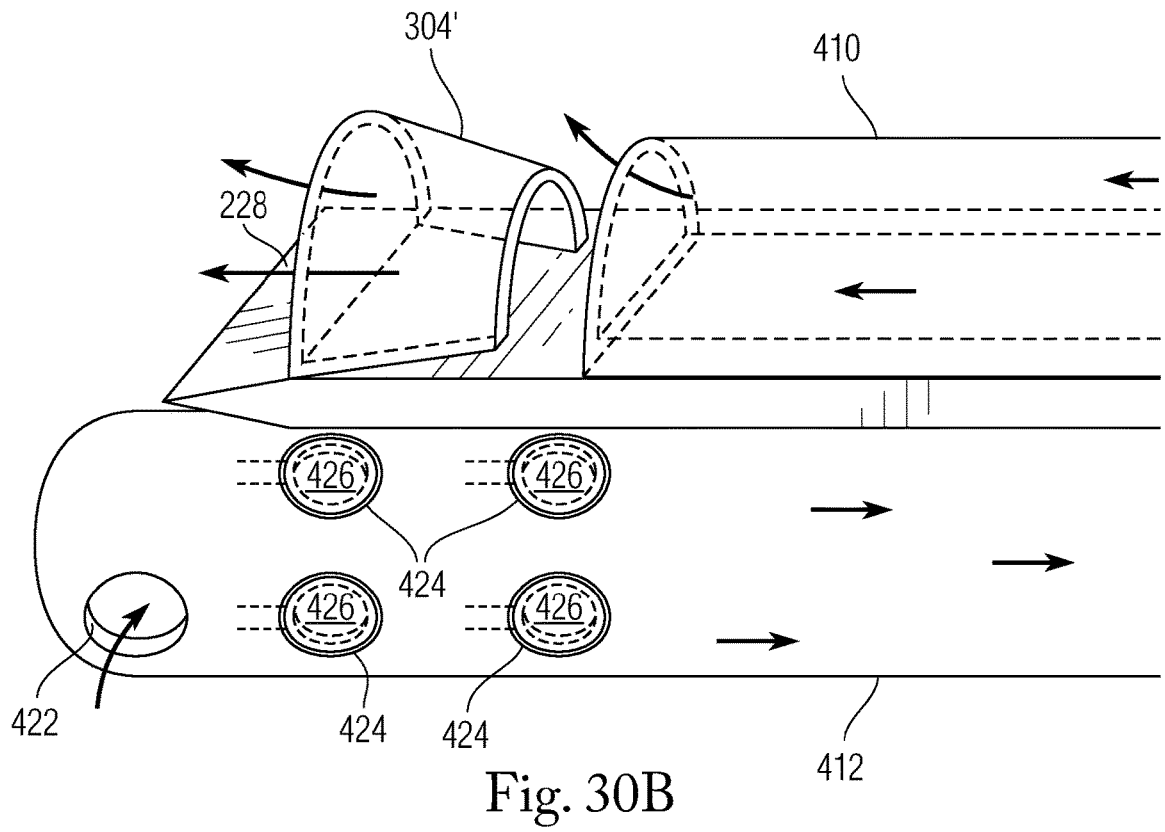

An alternative embodiment is shown in FIGS. 30A and 30B in which sleeve 430 is replaced with one-way valves 426 located across at least some of the openings 424. The purpose of the valves 426 is to allow irrigation fluid to flow to the surgical site through openings 424 during phacoemulsification (FIG. 30A), but to close off some or all of the openings 424 when fluid flow is reversed during I/A cleanup (FIG. 30B). Also, in this embodiment, the bottom tube 412 can be moved in the distal direction so that it extends beyond the blade as shown in FIG. 30B. Thus, during phacoemulsification, the shape edge 228 of the knife is free of the structure and can easily contact cataract tissue. However, during I/A clean up, when the bottom tube 412 is moved distally, the sharp edge of the knife is against the upper surface of portion 413 of the lower tube where it cannot harm other tissue during clean up.

Figure 28A:
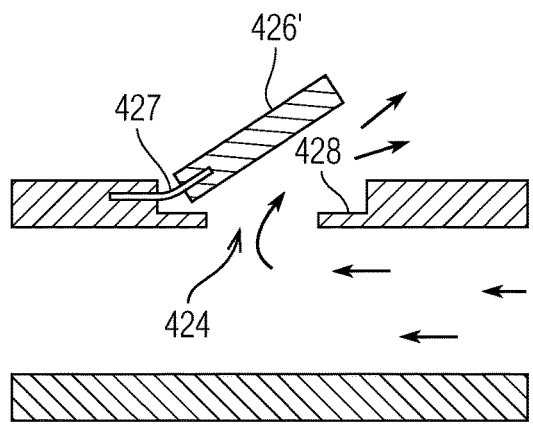
Figure 28B:
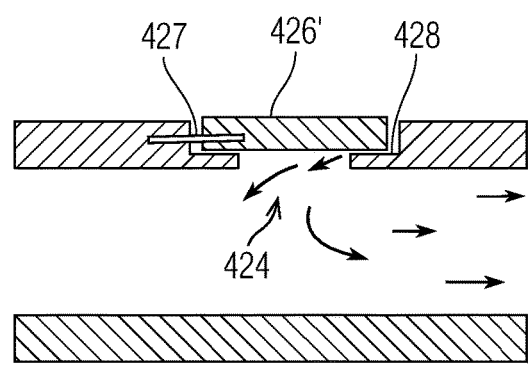

FIGS. 28A and 28B show a simple version of a one-way valve. One opening 424 is shown with a flap 426' adjacent it and fastened to the surrounding area by a spring wire hinge 427 that tends to keep the flap from sealing the opening 424. This spring 427 is aided in keeping the hole 424 open by the flow of irrigation fluid. During I/A clean up the fluid flow is reversed, and the aspiration fluid force tends to close the flap 426' against a ledge 428 at the rim of opening 424. Since no one-way valve is applied to hole 422, most aspiration fluid flows through it during I/A clean up. However, depending upon the aspiration force needed at hole 422, it may be desirable to leave some portion of the openings 424 open during clean up.

Figure 29A:
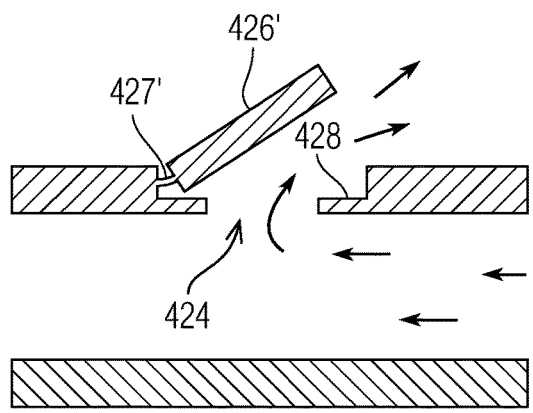
Figure 29B:
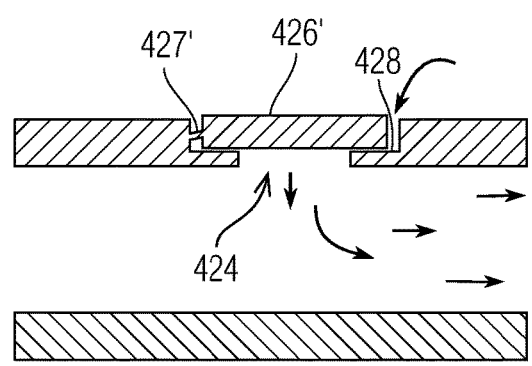

FIGS. 29A and 29B show an alternative form of the one-way valve. Instead of spring 427, each flap is merely attached to the rim of opening 424 by a piece 427' of the material of the sleeve. This material may impart some opening force on the flap 426', but the valve would still work without it based on the direction of fluid flow.

Figure 31:
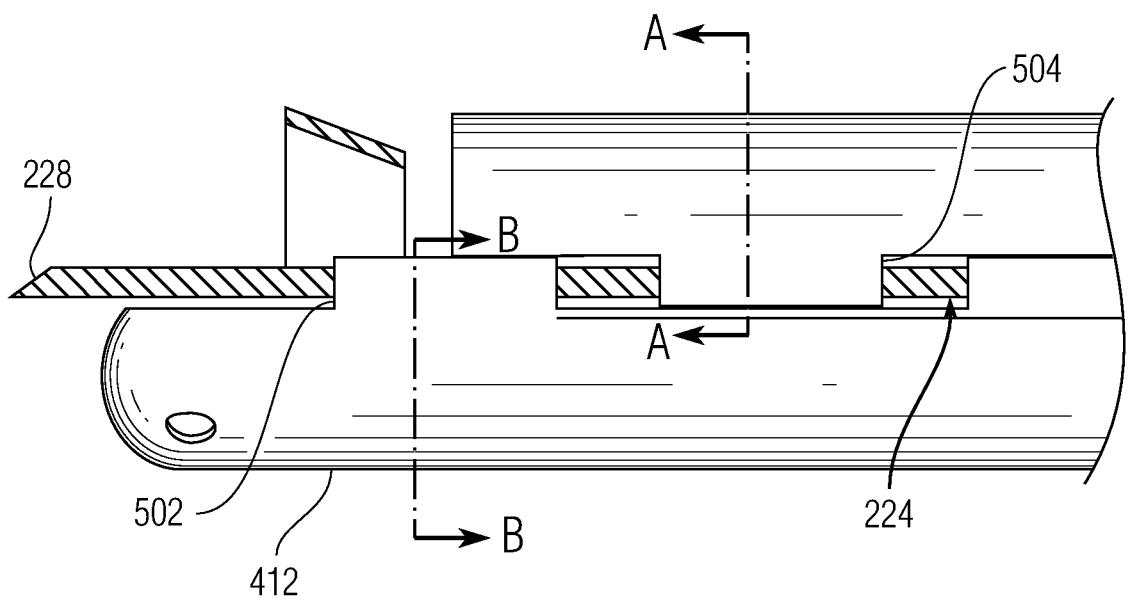
FIG. 31 is a longitudinal cross-sectional view of the modified embodiment of FIGS. 30A and B showing the knife variously captured by a channel in upper tube and a channel in the lower tube.
Figure 32A:
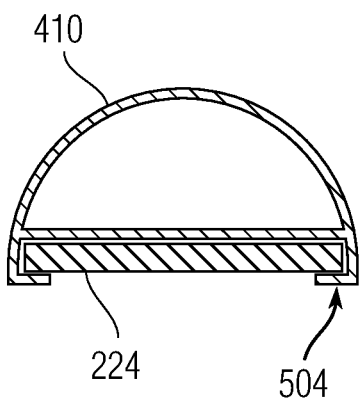
FIG. 32A is a transverse cross-sectional view of the work tip of FIG. 31 along line A-A.
Figure 32B:
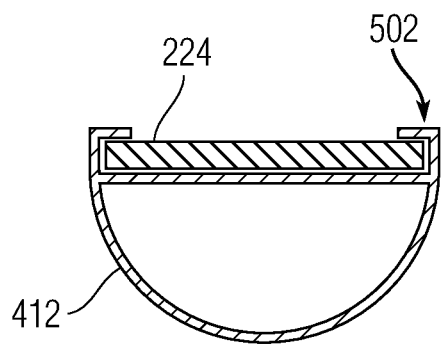
FIG. 32B is a transverse cross-sectional view of the work tip of FIG. 31 along line B-B.

The irrigation and aspiration tubes 410, 412 are stationary during phacoemulsification. It is only the blade 224 that is vibrated. As shown in the longitudinal cross section of FIG. 31 the stationary tubes can be supported with respect to the vibrating knife by means of channel 502 at the top of the lower fluid tube 412 and channel 504 at the bottom of the upper tube 410, which are aligned to capture the blade. FIG. 32A is a cross section at line A-A of FIG. 31 showing the channel 502 and FIG. 32B is a cross section at line B-B of FIG. 31 showing the channel 504.

Figure 33A:
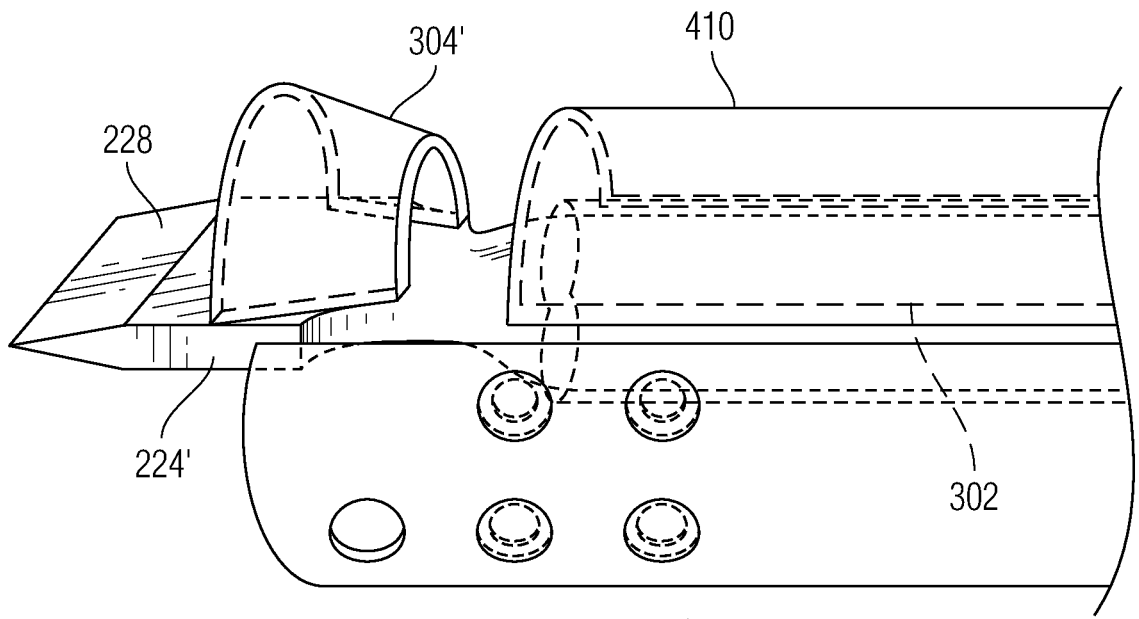
FIG. 33A shows the embodiment of FIG. 30A in which the knife has been modified to have a rod-like proximal end and FIG. 33B is a lateral cross-sectional view of FIG. 33A along line C-C.
Figure 33B:
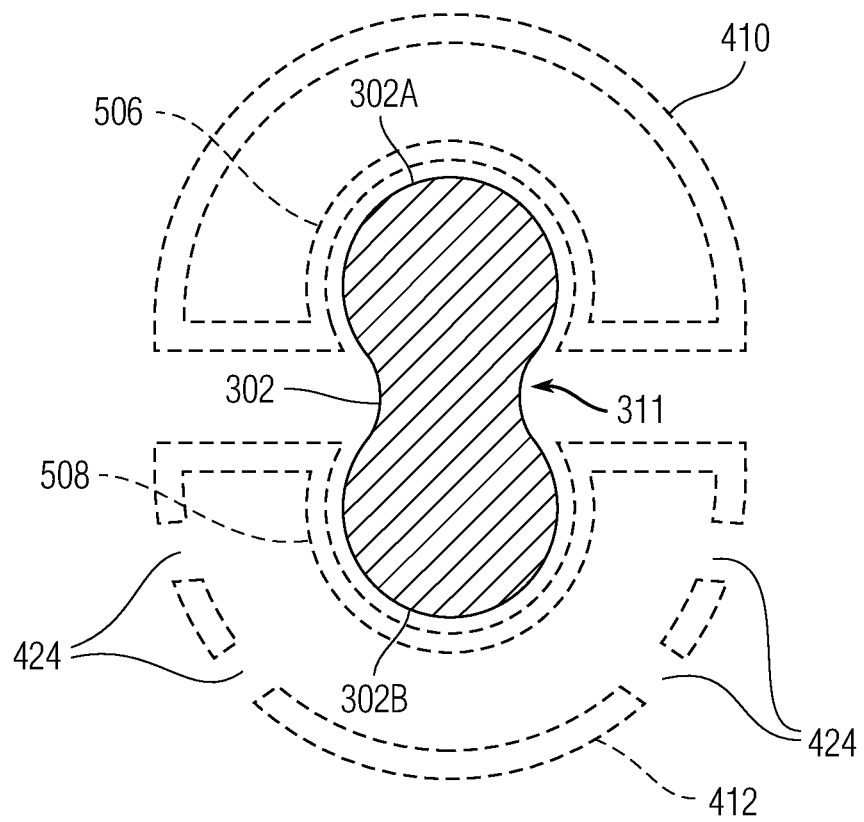

In the seventh, eighth or ninth embodiments blade 224 is shown as a flat blade of uniform rectangular cross section. However, it can be replaced with any of the blades shown in FIG. 8 or 10. FIG. 33A shows an embodiment similar to FIG. 30A, but in which the knife is like that in FIG. 10, but with a conical shaped collar 304'. In particular, the knife has a rod 302 extending from a flat blade portion 224'. As shown in the cross section of FIG. 33B, the rod has grooves 311 so as to divide the rod into top and bottom cylindrical sections. The top section 302A is captured in a cylindrical channel 506 in top fluid tube 410, while the bottom section 302B is captured in a cylindrical channel 508 in the bottom fluid tube 412. The rod vibrates in these channels, while the tubes remain stationary. It should be noted that in this embodiment the lower tube 412 can be slid forward so as to cover knife edge 228 during I/A clean up.

In one version of prior structures the fluid tubes were rigid, typically made of titanium, and were welded to and vibrated with the blade. In another version only the half hemispherical section 413 was made of metal. However, tubes 410 and 412 with the present embodiment may be made of rigid or flexible plastic materials because they are not vibrated and are not fixed to the blade. This results in a significant saving in the cost of materials and manufacturing.

The ring 304 and conical ring 304' are not required elements of the seventh, eighth or ninth embodiments and those embodiments can be operated successfully without them or any form of collar. Similarly, the half ring or collar 304 shown in these embodiments can be replaced with those in FIGS. 5-10. While the invention has been shown and described in connection with the removal of a cataract from the eye of a patient and subsequent I/A clean up, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the scope of the appended claims.

I claim:

1. A work tip for a surgical hand piece comprising:
a solid knife with a sharp distal end and opposing lateral surfaces over at least a part of the extent thereof;
a first fluid tube located on one of the lateral surfaces of the knife, said first fluid tube being located adjacent one lateral surface of the knife and having open ends to receive or discharge fluid; and
a second fluid tube located on the other of the lateral surfaces of the knife, said second fluid tube being slidably connected with the knife and having open ends to receive or discharge fluid, said second fluid tube having an opening at a distal end thereof on its surface that faces the knife, and having a side hole on a side of the tube at the distal end, wherein the side hole is smaller than the opening;
wherein during phacoemulsification the work tip can be placed in a phacoemulsification mode in which (a) the knife is adapted to be vibrated independent of the first and second tubes, (b) the second fluid tube is adapted to have irrigation fluid passed from its proximal end through the opening and side hole, (c) the second tube and knife are positioned so that the exit of irrigation fluid from the second fluid tube through the opening is not blocked and (d) the first fluid tube is positioned so as to receive fluid from the second tube that has passed about the knife, and
wherein during irrigation/aspiration (I/A) cleanup the work tip can be placed in an I/A clean up mode in which (a) the vibration of the knife is adapted to be slowed or stopped, (b) the second fluid tube is adapted to have aspiration fluid passed from its distal end through the side hole only, (c) the knife is positioned so as to block the aspiration fluid from entering the second fluid tube through the opening, and (d) the first fluid tube is adapted to provide irrigation fluid to its distal end, whereby I/A clean up is only through the side hole.

2. The work tip according to claim 1 wherein the knife further includes a half ring structure located distally of the first tube such that when in the phacoemulsification mode aspiration fluid entering the first tube is at least in part fluid that has passed through the half ring structure and when in the I/A clean up mode irrigation fluid passing out of the first tube is at least in part fluid that has passed through the half ring structure.

3. The work tip according to claim 2 wherein the first and second tubes have a half cylindrical shape with a flat side and the flat side of each is adjacent opposite lateral sides of the knife.

4. The work tip according to claim 2 wherein the half ring structure has a conical shape such that its diameter at its distal edge is larger than its diameter at its proximal edge.

5. The work tip according to claim 1 wherein the knife has a rectangular cross-sectional shape and the lateral sides are sides of the rectangular shape.

6. The work tip according to claim 1 wherein a proximal portion of the knife is a round rod.

7. The work tip according to claim 1 wherein the first and second tubes have a half cylindrical shape with a flat side and the flat side of each is adjacent opposite lateral sides of the knife.

8. The work tip according to claim 7 wherein the second tube has a half hemispherical region at its distal end.

9. The work tip according to claim 8 wherein the opening in the second tube is a half circular opening, and the hole and opening are in the half hemispherical region.

10. The work tip according to claim 9 wherein the knife further includes a half ring structure located distally of the first tube such that when in the phacoemulsification mode aspiration fluid entering the first tube is at least in part fluid that has passed through the half ring structure and when in the I/A clean up mode irrigation fluid passing out of the first tube is at least in part fluid that has passed through the half ring structure.

11. The work tip according to claim 1 wherein the second fluid tube has at least one internal groove adjacent to the opening at the distal end thereof that acts as a baffle to set a direction for fluid exiting the opening.

12. The work tip according to claim 11 wherein the second tube has a half hemispherical region at its distal end in which a plurality of the grooves are located to set separate directions for fluid exiting the opening.

13. The work tip according to claim 1 wherein during I/A clean up the second fluid tube can be slid distally with respect to the knife to cover the sharp distal end thereof.

14. The work tip according to claim 1 wherein the knife further includes a hole and wherein:
when in the phacoemulsification mode (a) the knife hole and the opening of the second tube are aligned so irrigation fluid passes from the proximal end of the second fluid tube through the opening, the side hole and the hole in the knife, (b) the second tube and knife are positioned so that the exit of irrigation fluid from the second fluid tube through the opening is not blocked and (c) the first fluid tube is positioned so as to receive fluid from the second tube that has passed through and about the knife, and
when in the I/A cleanup mode the knife is positioned so as to block the aspiration fluid from entering the second fluid tube through the opening and is proximal of the distal end of the second fluid tube.

15. The work tip according to claim 14 wherein the knife further includes a half ring structure located distally of the first tube such that when in the phacoemulsification mode aspiration fluid entering the first tube is at least in part fluid that has passed through the half ring structure and when in the I/A clean up mode irrigation fluid passing out of the first tube is at least in part fluid that has passed through the half ring structure.

16. The work tip according to claim 15 wherein the half ring structure has a conical shape such that its diameter at its distal edge is larger than its diameter at its proximal edge and the first fluid tube is positioned proximally of the half ring structure along a lateral surface of the knife.

17. The work tip according to claim 16 wherein (a) the second fluid tube has a half hemispherical region at its distal end, (b) the sharp distal end of the knife has a curved shape, (c) the sharp distal end of the knife extends distally beyond half hemispherical region at the distal end of the second fluid tube in the phacoemulsification mode, and (d) the sharp distal end of the knife is proximal of the half hemispherical region at the distal end of the second fluid tube in the I/A clean up mode.

18. The work tip according to claim 14 wherein a proximal portion of the knife is a round rod.

19. The work tip according to claim 14 wherein during I/A clean up the second fluid tube can be slid distally with respect to the knife to cover the sharp distal end thereof.

20. The work tip according to claim 1 wherein the first fluid tube has a channel adjacent one lateral surface of the knife in which the knife can vibrate.

21. The work tip according to claim 20 wherein the second fluid tube has a channel adjacent the other lateral surface of the knife in which the knife can vibrate.

22. The work tip according to claim 1 wherein the second fluid tube has a channel adjacent the other lateral surface of the knife in which the knife can vibrate.

23. The work tip according to claim 1 in which said solid knife has a rod forming a proximal portion thereof, said rod having groove on each side so as to divide the rod into upper and lower cylindrical sections, said first fluid tube having a cylindrical channel in a bottom portion thereof in which the upper cylindrical section of the rod is located so it can vibrate and said second fluid tube having a cylindrical channel in a top portion thereof in which the lower cylindrical section of the rod is located so it can vibrate, while the tubes remain stationary.

24. A work tip for a surgical hand piece comprising:
a solid knife with a sharp distal end and opposing lateral surfaces over at least a part of the extent thereof;
a first fluid tube located on one of the lateral surfaces of the knife, said first fluid tube having open ends to receive or discharge fluid;
a second fluid tube located on the other of the lateral surfaces of the knife, said second fluid tube having open ends to receive or discharge fluid, said second fluid tube having a plurality of openings at a distal end thereof on a side surface and having a side hole on the side surface more distal than the plurality of openings, wherein the side hole is smaller than the combination of the plurality of openings; and
a valve structure at the plurality of openings that can block fluid from being drawn into the second fluid tube through the plurality of openings;
wherein during phacoemulsification the work tip can be placed in a phacoemulsification mode in which (a) the knife is adapted to be vibrated independent of the first and second tubes, (b) the second fluid tube is adapted to have irrigation fluid passed from its proximal end through the plurality of openings and side hole, and (c) the first fluid tube is positioned so as to receive fluid from the second tube that has passed about the knife, and wherein during irrigation/aspiration (I/A) cleanup the work tip can be placed in an I/A clean up mode in which (a) the valve structure is adapted to block the entry of fluid into the plurality of openings, (b) the vibration of the knife is adapted to be reduced or stopped, (b) the second fluid tube is adapted to have aspiration fluid passed from its distal end through the side hole only, and (c) the first fluid tube is adapted to provide irrigation fluid to its distal end, whereby I/A clean up is only through the side hole.

25. The work tip according to claim 24 wherein the valve structure is a sleeve slidably located about the distal end of the second fluid tube, said sleeve being in a position and of sufficient extent that it can block all of the plurality of openings when the work tip is in an I/A clean up mode and can leave open the plurality of openings when in a phacoemulsification mode.

26. The work tip according to claim 24 wherein the valve structure is in the form of one-way valves at each of the plurality of openings arranged to allow fluid flow toward the distal end of the work tip and to block fluid flow toward the proximal end of the work tip.

27. The work tip according to claim 26 wherein the knife has a rectangular cross-sectional shape and the lateral sides are sides of the rectangular shape.

28. The work tip according to claim 24 wherein the knife further includes a half ring structure located distally of the first tube.

29. The work tip according to claim 28 wherein a proximal portion of the knife is a round rod.

30. The work tip according to claim 29 wherein the half ring structure has a conical shape such that its diameter at its distal edge is larger than its diameter at its proximal edge and the first fluid tube is positioned proximally of the half ring structure along a lateral surface of the knife.

31. The work tip according to claim 30 wherein the valve structure at each opening is a flap the size of the opening, a hinge that flexibly attaches the flap to the opening so as to block it and a ledge in the opening opposite the hinge, whereby fluid pushing in one direction causes the flap to swing about the hinge away from the opening and fluid pushing in the opposite direction causes the flap to swing about the hinge toward the opening until it contacts the ledge and closes the opening.

32. The work tip according to claim 31 wherein the hinge is a spring wire hinge.

33. The work tip according to claim 31 wherein the hinge is a piece of the material which the flap is made from.

34. The work tip according to claim 30 wherein during I/A clean up the second fluid tube can be slid distally with respect to the knife to cover the sharp distal end thereof.

* * * * *